US006506561B1

(12) United States Patent
Cheval et al.

(10) Patent No.: US 6,506,561 B1
(45) Date of Patent: Jan. 14, 2003

(54) METHOD OF OBTAINING A LIBRARY OF TAGS CAPABLE OF DEFINING A SPECIFIC STATE OF A BIOLOGICAL SAMPLE

(75) Inventors: Lydie Cheval, Saint-Michel-sur-Orge (FR); Jean-Marc Elalouf, Antony (FR); Bérangère Virlon, Sevres (FR)

(73) Assignees: Commissariat a l'Energie Atomique, Paris (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 09/301,721

(22) Filed: Apr. 29, 1999

(30) Foreign Application Priority Data

Jan. 27, 1999 (EP) .............................. 99400189

(51) Int. Cl.[7] .......................... C12P 19/34; C12Q 1/68; C07H 21/00
(52) U.S. Cl. ...................... 435/6; 435/91.1; 536/22.1; 536/24.2
(58) Field of Search .................. 435/6, 91.1; 536/22.1, 536/24.2; 935/1, 5, 6, 8, 9, 16, 19, 4

(56) References Cited

U.S. PATENT DOCUMENTS 5,597,815 A  * 1/1997  Deluca et al. ............... 514/167
5,695,937 A    12/1997  Kinzler et al. ................. 435/6
5,866,330 A  * 2/1999  Kinzler et al. ................. 435/6

FOREIGN PATENT DOCUMENTS

WO        00/44936        8/2000

OTHER PUBLICATIONS

Sambrook et al. Molecular cloning: construction and analysis of cDNA library. p. 8.11–8.17, 1984.*
Lee S, et al., Generation of high–quantity and quality tag/ditag cDNAs for SAGE analysis, Biotechniques Aug. 2001, vol. 31 (2), pp. 348–350, 352–354.
Datson NA et al., MicroSAGE: a modified procedure for serial analysis of gene expression in limited amounts of tissue, Nucleic Acids Res, Mar. 1999, vol. 27 (5), pp. 1300–1307.
Ye SQ et al., miniSAGE: gene expression profiling using serial analysis of gene expression from 1 microg total RNA, Anal Biochem Dec. 2000, vol. 287 (1), pp. 144–152.
Brad St. Croix et al., MicroSAGE Detailed Protocol, Version 1.0, Jun. 22, 2000, pp. 1–26.
Johns Hopkins Oncology Center, Appendix D: Frequently asked questions and answers, letter dated Sep. 10, 1997 from Victor E. Velculescu.
NA Datson et al., Oxford Journals Online, MicroSAGE: *a modified procedure* for serial analysis of gene expression *in limited amounts of tissue*, Jan. 14, 1999, pp. 1300–1307.
Scott Augenstein, Superparamagnetic beads: Applications of solid–phase RT–PCR, May 1994, pp. 12–13.

(List continued on next page.)

Primary Examiner—Kenneth R. Horlick
Assistant Examiner—Joyce Tung
(74) Attorney, Agent, or Firm—Oblon, Spivak, McClelland, Maier & Neustadt, P.C.

(57) ABSTRACT

A method of obtaining a library of tags able to define a specific state of a biological sample, such as a tissue or a cell culture. The present method provides an important advantage over other methods used to analyze gene expression in that libraries may be generated from tiny amounts of cells, e.g., from 30,000–100,000 cells.

19 Claims, 5 Drawing Sheets

OTHER PUBLICATIONS

Bérangére Virlon et al., Serial microanalysis of renal transcriptomes, PNAS, Dec. 21, 1999, vol. 96, No. 26, pp. 15286–15291.

Shui Qing Ye et al., MiniSAGE: Gene Expression Profiling Using Serial Analysis of Gene Expression from 1 μg Total RNA, Analytical Biochemistry, 287, 144–152 (2000).

David G. Peters et al., Comprehensive transcript analysis in small quantities of mRNA by SAGE–Lite, Nucleic Acids Research, 1999, vol. 27, No. 24.

Brad St. Croix et al., Genes Expressed in Human Tumor Endothelium, www.sciencemag.org, Science vol. 289, Aug. 18, 2000, pp. 1197–1202.

N.A. Datson et al., MicroSAGE: a modified procedure for serial analysis of gene expression in limited amounts of tissue, Nucleic Acids Research, 1999, vol. 27, No. 5, pp. 1300–1307.

Arthur H. Bertesen et al., High–throughput gene expression analysis using SAGE, DDT vol. 3, No. 4, Apr. 1998, pp. 152–159.

Jes Stellberg et al., A Quantitative Evaluation of SAGE, Geonome Research, www.geoneme.orge, 2000 vol. 10(8), pp. 1241–1248.

Richard A. Shimkets et al., Gene expression analysis by transcript profiling coupled to a gene database query, Nature Biotechnology, vol. 17, Aug. 1999, pp. 798–803.

Mark D. Adams, Serial analysis of gene expression: ESTs get smaller, BioEssays, 1996, vol. 18, No. 4, pp. 261–262.

Heiko Hermeking et al., 14–3–3o Is a p53–Regulated Inhibitor of G2/M Progression, Molecular Cell, vol. 1, 3–11, Dec. 1997.

J. Powell, Enhanced concatemer cloning–a modification to the SAGE (Serial Analysis of Gene Expression) technique, Nucleic Acids Research, 1998, Vo. 26, No. 14, pp. 3445–3446.

Expressions, Powerful genome–wide expression analysis, vol. 8, issue 1, Feb. 2001.

Victor E. Velculescu et al., Serial Analysis of Gene Expression, Science, vol. 270, Oct. 20, 1995, pp. 484–487.

Johanne M. Kaplan et al., Induction of Antitumor Immunity with Dendritic Cells Transduced with Adenovirus Vector–Encloding Endogenous Tumor–Associated Antigens, The Journal of Immunology, 1999, pp. 699–707.

James Kling, Technology Provides Quick Access to DNA Data, Differential Gene Expression, The Scientist, Aug. 31, 1998.

Victor E. Velculescu et al., Analysing uncharted transcriptomes with SAGE, TIG Oct. 2000, vol. 16, No. 10, pp. 423–425.

Anita Lal, A Public Database for Gene Expression in Human Cancers, Cancer Research 59, 5403–5407, Nov. 1, 1999.

M. Kenzelmann et al., Substantially enhanced cloning efficiency of SAGE (Serial Analysis of Gene Expression) by adding a heating step to the original protocol, Nucleic Acids Research, 1999, vol. 27, No. 3, pp. 917–918.

Gregory D. Schuler; Pieces of the puzzle; expressed sequence tags and the catalog of human genes, Bioinformatics: Bits and Bytes pp. 694–698 1997, J. Med. Med. vol. 75(2).

Stéphane Audic, The Significance of Digital Gene Expression Profiles, Genome Research, pp. 996–995.

Anke van den Berg, Serial analysis of gene expression: rapid RT–PCR analysis of unknown SAGE tags, Nucleic Acids Research, 1999, vol. 27, No. 17.

* cited by examiner

SEQUENCE LISTING

<160> NUMBER OF SEQ ID NOS: 28

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence:synthetic DNA
<221> NAME/KEY: misc_feature
<222> LOCATION: (40)..(46)
<223> OTHER INFORMATION: nucleotides 40 to 46 are optionally present

```
<223> OTHER INFORMATION: n at positions 10 through 46 are a, c, g, or t

<400> SEQUENCE: 1
gatcgtcccn nnnnnnnnnn nnnnnnnnnn nnnnnnnnnn nnnnnn            46

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence:synthetic
      DNA
<221> NAME/KEY: misc_feature
<222> LOCATION: (40)..(46)
<223> OTHER INFORMATION: nucleotides 40 through 46 are optionally
      present
<223> OTHER INFORMATION: n at positions 10 through 46 are a, c, g, or t

<400> SEQUENCE: 2
gatcgtcccn nnnnnnnnnn nnnnnnnnnn nnnnnnnnnn nnnnnn            46

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
ttttgccagg tcactcaagt cggtcattca tgtcagcaca gggac             45

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
gatcgtccct gtgctgacat gaatgaccga cttgagtgac ctggca            46

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
tttttgctca ggctcaaggc tcgtctaatc acagtcggaa gggac             45

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
gatcgtccct tccgactgtg attagacgag ccttgagcct gagcaa            46

<210> SEQ ID NO 7
<211> LENGTH: 23
```

```
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
gccaggtcac tcaagtcggt cat                                             23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8
tgctcaggct caaggctcgt cta                                             23

<210> SEQ ID NO 9
<211> LENGTH: 10
<212> TYPE: DNA
<213> ORGANISM: Mus musculus

<400> SEQUENCE: 9
gtggcagtgg                                                            10

<210> SEQ ID NO 10
<211> LENGTH: 10
<212> TYPE: DNA
<213> ORGANISM: Mus musculus

<400> SEQUENCE: 10
ttataatttg                                                            10

<210> SEQ ID NO 11
<211> LENGTH: 10
<212> TYPE: DNA
<213> ORGANISM: Mus musculus

<400> SEQUENCE: 11
tggcagtggg                                                            10

<210> SEQ ID NO 12
<211> LENGTH: 10
<212> TYPE: DNA
<213> ORGANISM: Mus musculus

<400> SEQUENCE: 12
tgactccctc                                                            10

<210> SEQ ID NO 13
<211> LENGTH: 10
<212> TYPE: DNA
<213> ORGANISM: Mus musculus

<400> SEQUENCE: 13
aagtttaaat                                                            10

<210> SEQ ID NO 14
<211> LENGTH: 10
<212> TYPE: DNA
<213> ORGANISM: Mus musculus
```

-continued

<400> SEQUENCE: 14 agcaagcagg					10

<210> SEQ ID NO 15
<211> LENGTH: 10
<212> TYPE: DNA
<213> ORGANISM: Mus musculus

<400> SEQUENCE: 15 caaaaagcta					10

<210> SEQ ID NO 16
<211> LENGTH: 10
<212> TYPE: DNA
<213> ORGANISM: Mus musculus

<400> SEQUENCE: 16 accgaccgca					10

<210> SEQ ID NO 17
<211> LENGTH: 10
<212> TYPE: DNA
<213> ORGANISM: Mus musculus

<400> SEQUENCE: 17 accgaccgca					10

<210> SEQ ID NO 18
<211> LENGTH: 10
<212> TYPE: DNA
<213> ORGANISM: Mus musculus

<400> SEQUENCE: 18 cagaagaagt					10

<210> SEQ ID NO 19
<211> LENGTH: 10
<212> TYPE: DNA
<213> ORGANISM: Mus musculus

<400> SEQUENCE: 19 aaataaagtt					10

<210> SEQ ID NO 20
<211> LENGTH: 10
<212> TYPE: DNA
<213> ORGANISM: Mus musculus

<400> SEQUENCE: 20 agaagcagtg					10

<210> SEQ ID NO 21
<211> LENGTH: 10
<212> TYPE: DNA
<213> ORGANISM: Mus musculus

<400> SEQUENCE: 21 tgatgccctc					10

<210> SEQ ID NO 22
<211> LENGTH: 10
<212> TYPE: DNA
<213> ORGANISM: Mus musculus

```
-continued

<400> SEQUENCE: 22
aggctactac                                                              10

<210> SEQ ID NO 23
<211> LENGTH: 10
<212> TYPE: DNA
<213> ORGANISM: Mus musculus

<400> SEQUENCE: 23
gctcattgga                                                              10

<210> SEQ ID NO 24
<211> LENGTH: 10
<212> TYPE: DNA
<213> ORGANISM: Mus musculus

<400> SEQUENCE: 24
gctttcagca                                                              10

<210> SEQ ID NO 25
<211> LENGTH: 10
<212> TYPE: DNA
<213> ORGANISM: Mus musculus

<400> SEQUENCE: 25
gtgactgggt                                                              10

<210> SEQ ID NO 26
<211> LENGTH: 10
<212> TYPE: DNA
<213> ORGANISM: Mus musculus

<400> SEQUENCE: 26
tgaccaaggc                                                              10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 27
gtccctgtgc                                                              10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
gtcccttccg                                                              10
```

METHOD OF OBTAINING A LIBRARY OF TAGS CAPABLE OF DEFINING A SPECIFIC STATE OF A BIOLOGICAL SAMPLE

BACKGROUND OF THE INVENTION

1. Field of the Invention

The present invention relates to methods of analyzing gene expression that require only small amounts of biological samples.

2. Description of the Background

Several methods are now available for monitoring gene expression on a genomic scale. These include DNA microarrays (1, 2) and macroarrays (3, 4), expressed sequence tag (EST) determination (5, 6), and serial analysis of gene expression (7). Such methods have been designed, and are still used, for analyzing macroamounts of biological material (1–5 µg of poly(A) mRNAs, i.e. ~$10^7$ cells). However, mammalian tissues consist of several different cell types with specific physiological functions and gene expression patterns. Obviously, this makes intricate the interpretation of large scale expression data in higher organisms. It is therefore most desirable to set out methods suitable for the analysis of defined cell populations.

SAGE has been shown to provide rapid and detailed information on transcript abundance and diversity (7–10). It involves several steps for mRNA purification, cDNA tags generation and isolation, and PCR amplification. It was reasoned that increasing the yield of the various extraction procedures, together with slight modifications in the number of PCR cycles could enlarge SAGE potentiality.

SAGE was first described by Velculescu et al. in 1995 (U.S. Pat. No. 5,695,937 (incorporated herein by reference, and ref. 7), and rests on 3 principles which have now been all corroborated experimentally: a) short nucleotide sequence tags (10 bp) are long enough to be specific of a transcript, especially if they are isolated from a defined portion of each transcript; b) concatenation of several tags within a single DNA molecule greatly increases the throughput of data acquisition; c) the quantitative recovery of transcript specific tags allows to establish representative gene expression profiles.

However, this method was designed to study macroamounts of biological materials (5 µg of poly(A) RNAs, i.e. about $10^7$ cells). Since mammalian tissues consist of several different cell types with specific physiological functions and gene expression patterns, it is most desirable to scale down the SAGE approach for studying well delineated tissue fragments or isolated cell populations.

According, there remains a need for a process that may be conducted using smaller amounts of the biological sample as compared to the SAGE method described above.

SUMMARY OF THE INVENTION

It is an object of the present invention to provide a method of analyzing gene expression which requires only small quantities of biological samples.

The present invention is based on the discovery of a microadaptation of SAGE, referred to herein as SADE since, in contrast to SAGE, the inventive method described herein provides quantitative gene expression data on a small number (30,000–50,000) of cells.

The object of the present invention above, and others, may be accomplished with a method of obtaining a library of tags able to define a specific state of a biological sample, such as a tissue or a cell culture, comprising the following successive steps:

(1) extracting in a single-step mRNA from a small amount of a biological sample using an oligo(dT), e.g., oligo $(dT)_{25}$, covalently bound to paramagnetic beads, (2) generating a double-strand cDNA library, from the mRNA according to the following steps:
   (a) synthesizing the $1^{st}$ strand of the cDNA by reverse transcription of the mRNA template into a 1st complementary single-strand cDNA, using a reverse transcriptase lacking Rnase H activity,
   (b) synthesizing the 2nd strand of the cDNA by nick translation of the mRNA, in the mRNA-cDNA hybrid form by an *E. coli* DNA polymerase, (3) cleaving the obtained cDNAs with an anchoring enzyme, corresponding to a restriction endonuclease with a 4-bp recognition site, (4) separating the cleaved cDNAs in two aliquots, (5) linking or ligating the cDNA contained in each of the two aliquots with different oligonucleotide linkers comprising a type IIS recognition site, (6) digesting the products obtained in step (5) with a type IIS restriction enzyme and obtaining two different tags, (7) blunt-ending the tags with a DNA polymerase, e.g., T7 DNA polymerase or Vent polymerase, and mixing the tags ligated with the different linkers, (8) ligating the tags obtained in step (7) to form ditags with a DNA ligase, and (9) determining the nucleotide sequence of at least one tag of the ditag to detect gene expression.

The object of the invention may also be accomplished with a more specific method of obtaining a library of tags able to define a specific state of a biological sample, such as a tissue or a cell culture, comprising the following successive steps:

(1) extracting in a single-step mRNA from a small amount of a biological sample using an oligo(dT), e.g., oligo $(dT)_{25}$, covalently bound to paramagnetic beads, (2) generating a double-strand cDNA library, from the mRNA according to the following steps:
   (a) synthesizing the 1st strand of the cDNA by reverse transcription of the mRNA template into a 1st complementary single-strand cDNA, using a reverse transcriptase lacking Rnase H activity,
   (b) synthesizing the 2nd strand of the cDNA by nick translation of the mRNA, in the mRNA-cDNA hybrid form by an *E. coli* DNA polymerase, (3) cleaving the obtained cDNAs using the restriction endonuclease Sau3A I as anchoring enzyme, (4) separating the cleaved cDNAs in two aliquots, (5) ligating the cDNA contained in each of the two aliquots via the Sau3A I restriction site to a linker consisting of one double-strand cDNA molecule having one of the following formulas:

GATCGTCCC-$X_1$ SEQ ID NO:1 or GATCGTCCC-$X_2$ SEQ ID NO:2, wherein $X_1$ and $X_2$, which comprise 30–37 nucleotides and are different, include a 20–25 bp PCR priming site with a Tm of 55° C.–65° C., and wherein GATCGTCCC corresponds to a Sau3A I restriction site joined to a BsmF I restriction site, (6) digesting the products obtained in step (5) with the tagging enzyme BsmF I and releasing linkers with anchored short piece of cDNA corresponding to a transcript-specific tag, the digestion generating BsmF I tags specific of the initial mRNA, (7) blunt-ending the BsmF I tags with a DNA polymerase, preferably T7 DNA polymerase or Vent polymerase and mixing the tags ligated with the different linkers, (8) ligating the tags obtained in step (7) to form ditags with a DNA ligase, (9) amplifying the ditags obtained in step (8) with primers comprising 20–25 bp and having a Tm of 55°–65° C.,

(10) isolating the ditags having between 20 and 28 bp from the amplification products obtained in step (9) by digesting the amplification products with the anchoring enzyme Sau3A I and separating the digested products on an appropriate gel electrophoresis,

(11) ligating the ditags obtained in step (10) to form concatemers, purifying the concatemers and separating the concatemers having more than 300 bp,

(12) cloning and sequencing the concatemers and

(13) analyzing the different obtained tags.

The object of the present invention is also accomplished with the use of a library of tags obtained according to the methods described above, for assessing the state of a biological sample, such as a tissue or a cell culture.

The present invention also includes the use of the tags obtained according to the methods described above as probes.

The subject of the present invention is also a method of determining a gene expression profile, comprising:

performing one of the here above defined methods and translating cDNA tag abundance in gene expression profile.

The present invention also includes to a kit useful for detection of gene expression profile, characterized in that the presence of a cDNA tag, obtained from the mRNA extracted from a biological sample, is indicative of expression of a gene having the tag sequence at an appropriate position, i.e. immediately adjacent to the most 3' Sau3A I site in the cDNA, obtained from the mRNA, the kit comprising further to usual buffers for cDNA synthesis, restriction enzyme digestion, ligation and amplification, containers containing a linker consisting of one double-strand cDNA molecule having one of the following formulas:

GATCGTCCC-$X_1$ SEQ ID NO:1 or GATCGTCCC-$X_2$ SEQ ID NO:2, wherein $X_1$ and $X_2$, which comprise 30–37 nucleotides and are different, include a 20–25 bp PCR priming site with a Tm of 55° C.–65° C., and wherein GATCGTCCC corresponds to a Sau3A I restriction site joined to a BsmF I restriction site, and containers containing primers comprising 20–25 bp and having a Tm of 55° 65° C.

As compared to SAGE, the inventive SADE method includes the following features: 1) single-step mRNA purification from tissue lysate; 2) use of a reverse transcriptase lacking Rnase H activity; 3) use of a different anchoring enzyme; 4) modification of procedures for blunt-ending cDNA tags; and 5) design of new linkers and PCR primers.

FIG. 1, modified from the original studies of Velculescu et al., summarizes the different steps of the SADE method, which is a microadaptation of SAGE. Briefly, as described above, mRNAs are extracted using oligo(dT)$_{25}$, covalently bound to paramagnetic beads. Double strand cDNA is synthesized from mRNA using oligo(dT)$_{25}$ as primer for the 1st strand synthesis. The cDNA is then cleaved using a restriction endonuclease (anchoring enzyme: Sau3A I) with a 4-bp recognition site. Since such an enzyme cleaves DNA molecules every 256 bp (44) on average, virtually all cDNAs are predicted to be cleaved at least once. The 3' end of each cDNA is isolated using the property of the paramagnetic beads and divided in half. Each of the two aliquots is ligated via the anchoring enzyme restriction site to one of the two linkers containing a type IIS recognition site (tagging enzyme: BsmF I) and a priming site for PCR amplification. Type IIS restriction endonucleases display recognition and cleavage sites separated by a defined length (14 bp for BsmF I), irrespective of the intercalated sequence. Digestion with the type IIS restriction enzyme thus releases linkers with an anchored short piece of cDNA, corresponding to a transcript-specific tag. After blunt ending of tags, the two aliquots are linked together and amplified by PCR. Since all targets are of the same length (110 bp) and are amplified with the same primers, potential distortions introduced by PCR are greatly reduced. Furthermore, these distortions can be evaluated, and the data corrected accordingly (7, 8). Ditags present in the PCR products are recovered through digestion with the anchoring enzyme and gel purification, then concatenated and cloned.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
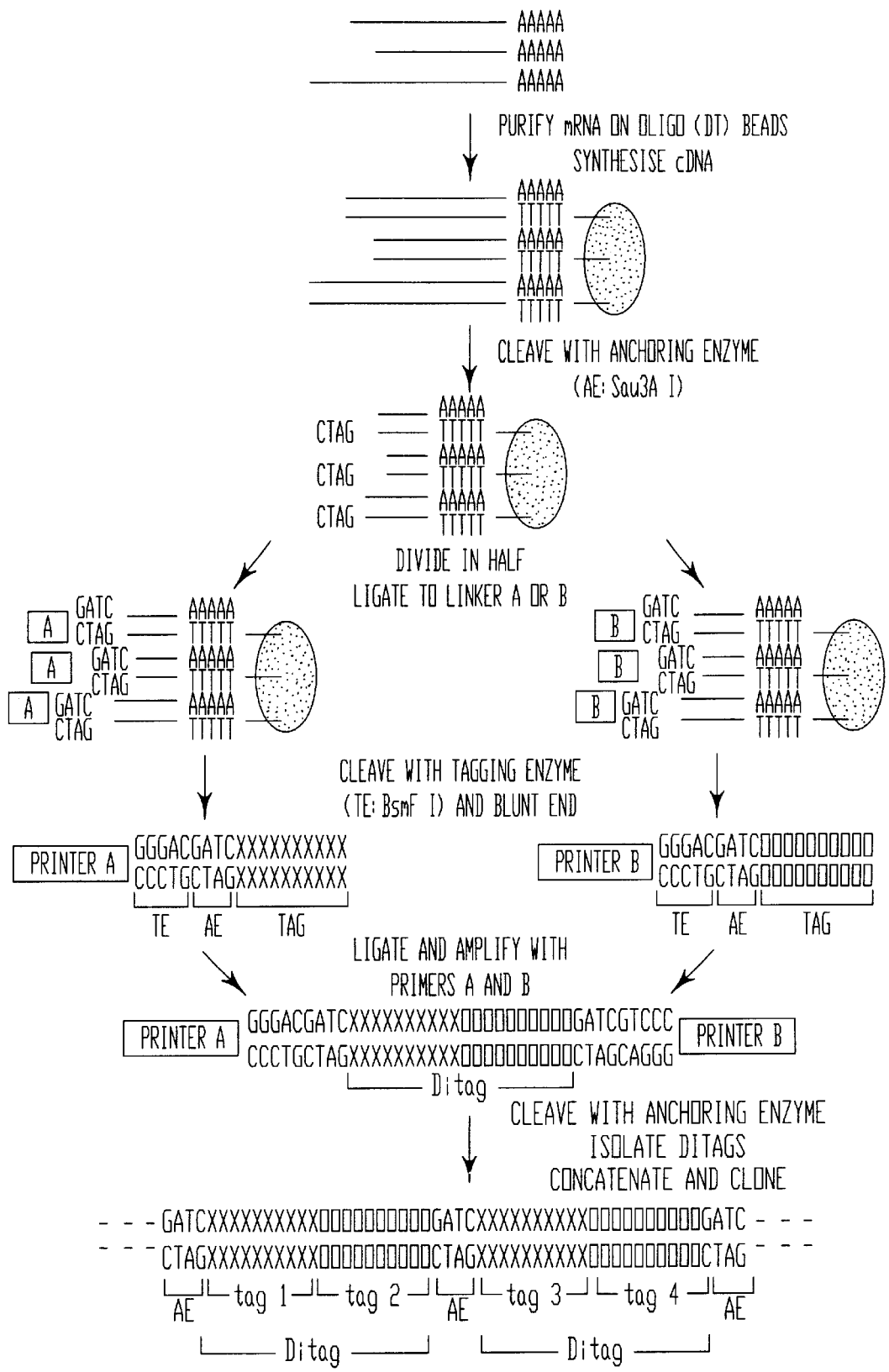
FIG. 1 is an outline of procedures for constructing SADE libraries. Poly(A) RNAs are isolated from tissue lysate using oligo(dT)$_{25}$ covalently linked to paramagnetic beads, and cDNA is synthesized under solid-phase condition. Bold face characters correspond to biologically relevant sequences, whereas light characters represent linker-derived sequences. The anchoring enzyme (AK) is Sau3A I, whereas the tagging enzyme (TE) is BsmF I. See text for details.

Unexpectedly, the following features of the present method: 1) single-step mRNA purification from tissue lysate using oligo(dT) covalently bound to paramagnetic beads; 2) use of a reverse transcriptase lacking Rnase H activity; and 3) modification of procedures for blunt-ending cDNA tag, allows the generation of libraries from tiny amounts of cells, i.e. from 30,000–100,000 cells.

In the SAGE method, mRNAs are isolated using conventional methods, then hybridized to biotinylated oligo(dT) for cDNA synthesis. After cleavage with the anchoring enzyme Nla III, the biotinylated cDNA fraction (3' end) is purified by binding to streptavidin beads.

In the inventive SADE method described herein, mRNAs are directly isolated from the tissue lysate through hybridization to oligo(dT) covalently bound to magnetic beads. Then, all steps of the experiment (until step 3 of protocol 5, as described hereafter) are performed on magnetic beads. This procedure saves time for the initial part of the experiment and, more importantly, provides better recovery. Quantitative analysis of the cDNA amounts available for library construction revealed dramatic differences between SAGE and SADE. With the SAGE method, starting from 500 mg tissue, 1.7 $\mu$g of cDNA are obtained, and only 4 ng were able to bind to streptavidin beads after Sau3A I digestion. With the SADE method, starting from 250 mg of tissue, 3.2 $\mu$g of cDNA were synthesized on beads, and 0.5 $\mu$g remained bound after Sau3A I cleavage. The increased yield of SADE (X250) explains the success in constructing libraries from as few as 30,000 cells. Using different sources of oligo(dT) leaded to poor cDNA recoveries. This may be explained by the fact that the binding capacity of streptavidin beads can be altered by several parameters, such as the presence of phenol, the length and composition of the biotinylated DNA fragments, and the length of the spacer between the oligo (dT) and the biotin molecule.

Another important difference between SAGE and SADE concerns the selected anchoring enzyme. Although any restriction enzyme with a 4-bp restriction site could serve as anchoring enzyme, Sau3A I may be preferred to Nla III (7–10) or other enzymes. Several cDNA libraries used for large scale sequencing are constructed by vector priming, followed by cDNA cleavage with Mbo I (an isoschizomer of Sau3A I which does not cut the vector (methylated) DNA), and circularization (6). SADE tags therefore correspond to the cDNA 5' ends of these libraries, which enables to use more efficiently EST data bases to analyze the data.

According to an advantageous embodiment of the method, in step (1), after mRNA binding to beads, different washes are performed in washing buffer supplemented with glycogen; such an addition avoids loss of the material; this may be important when starting from low amount of tissues.

According to another advantageous embodiment of the method, the two different oligonucleotide linkers further comprise amplification primer hybridization sequences, and the method further comprises amplifying the ditags.

According to yet another advantageous embodiment of the method, step (9) comprises producing and cloning concatemers of the ditags, preferably having more than 300 bp.

According to an advantageous embodiment of the method, in step (1), after mRNA binding to beads, different washes are performed in washing buffer supplemented with glycogen; such an addition avoids loss of the material; this may be important when starting from low amount of tissues.

According to an other advantageous embodiment of the method, in step (2), the synthesis of the 1st strand of the cDNA is performed with Moloney Murine Leukaemia Virus reverse transcriptase (M-MLV RT), and oligo(dT)$_{25}$ as primers.

According to yet another advantageous embodiment of the method, the linkers of step (5) are preferably hybrid DNA molecules formed from linkers 1A and 1B or from linkers 2A and 2B, having the following formulas:

linker 1A: 5'-TTTTGCCAGGTCACTCAAGTCGGTCAT-TCATGTCAGCACAGGGAC-3' (SEQ ID NO:3)

linker 1B: 5'-GATCGTCCCTGTGCTGACATGAATGAC-CGACTTGAGTGACCTGGCA-3' (SEQ ID NO:4)

or linker 2A: 5'-TTTTTGCTCAGGCTCAAG-GCTCGTCTAATCACAGTCGGAAGGGAC-3' (SEQ ID NO:5)

linker 2B: 5'-GATCGTCCCTTCCGACTGTGATTAGAC-GAGCCTTGAGCCTGAGCAA-3' (SEQ ID NO:6).

According to another advantageous embodiment of the method, the amount of each linker in step (5) is at most of 8–10 pmol and preferably comprised between 0.5 pmol and 8 pmol for initial amounts of respectively 10–40 ng of mRNAs and 5 $\mu$g of mRNAs.

According to yet another advantageous embodiment of the method, the primers of step (9) have preferably the following formulas:

5'-GCCAGGTCACTCAAGTCGGTCATT-3' (SEQ ID NO:7)

5'-TGCTCAGGCTCAAGGCTCGTCTA-3' (SEQ ID NO:8).

According to yet another advantageous embodiment of the method, the biological sample of step (1) preferably, comprises <5·10$^6$ cells, corresponding to at most 50 $\mu$g of total RNA or 1 $\mu$g of poly(A) RNA.

According to the invention, biological sample means for instance: tissue, cells (native or cultured cells), which are lysed for extracting mRNA.

According to another advantageous embodiment of the method, the tissue sample is from kidney, more specifically from nephron segments corresponding to about 15,000 to 45,000 cells, corresponding to 0.15–0.45 $\mu$g of total RNA.

According to a preferred embodiment of the method the gene expression profile obtained in mouse outer medullary collecting duct (OMCD) and in mouse medullary thick ascending limb (MTAL) is as specified in Table I below:

| OMCD | MTAL | Tag | GenBank match |
|---|---|---|---|
| 99 | 2 | GTGGCAGTGG | EST (AA097074) similar to rat AQP-2 (D13906) (SEQ ID NO: 9) |
| 34 | 1 | TTATAATTTG | ESTs (SEQ ID NO: 10) |
| 27 | 0 | TGGCAGTGGG | No match (SEQ ID NO: 11) |
| 19 | 5 | TGACTCCCTC | B2 repetitive sequence (SEQ ID NO: 12) |
| 13 | 0 | AAGTTTAAAT | Thymosin beta-4 (X16053) (SEQ ID NO: 13) |
| 13 | 1 | AGCAAGCAGG | 13-actin (X03672) |
| 13 | 4 | CAAAAAGCTA | ESTs, similar to rat ribosomal protein L11 (X62146) (SEQ ID NO: 15) |
| 11 | 1 | ACATTCCTTA | ESTs (SEQ ID NO: 16) |
| 11 | 14 | ACCGACCGCA | Integral membrane protein 2B1 (U76253) (SEQ ID NO: 17) |
| 11 | 0 | CAGAAGAAGT | Endogenous murine leukemia virus M17326) (SEQ ID NO: 18) |
| 10 | 5 | AAATAAAGTT | Lactate deshydrogenase 2, B chain (X51905) (SEQ ID NO: 19) |
| 10 | 0 | AGAAGCAGTG | EST 750555 (AA472938) (SEQ ID NO: 20) |
| 10 | 6 | TGATGCCCTC | B2 repetitive sequence (SEQ ID NO: 21) |
| 9 | 4 | AGGCTACTAC | Ribosomal protein L27a (X05021) (SEQ ID NO: 22) |
| 9 | 11 | GCTCATTGGA | ESTs (SEQ ID NO: 23) |
| 9 | 6 | GCTTTCAGCA | ESTs, similar to human extracellular proteinase inhibitor homologue (X63187) (SEQ ID NO: 24) |
| 9 | 14 | GTGACTGGGT | CytC oxidase subunit IV (X54691) (SEQ ID NO: 25) |
| 9 | 0 | TGACCAAGGC | 11 β-hydroxysteroid dehydrogenase type 2 X90647) (SEQ ID NO: 26) |

According to an advantageous embodiment of the kit, it preferably contains containers containing hybrid DNA molecules formed from linkers 1A and 1B or from linkers 2A and 2B, having the following formulas:

linker 1A: 5'-TTTTGCCAGGTCACTCAAGTCGGTCAT-TCATGTCAGCACAGGGAC-3' (SEQ ID NO:3)

linker 1B: 5 '-GATCGTCCCTGTGCTGACATGAATGAC-CGACTTGAGTGACCTGGCA-3' (SEQ ID NO:4)

or linker 2A: 5'-TTTTTGCTCAGGCTCAAG-GCTCGTCTAATCACAGTCGGAAGGGAC-3' (SEQ ID NO:5)

linker 2B: 5'-GATCGTCCCTTCCGACTGTGATTAGAC-GAGCCTTGAGCCTGAGCAA-3' (SEQ ID NO:6), and containers containing the following primers:

5'-GCCAGGTCACTCAAGTCGGTCATT-3' (SEQ ID NO:7)

5'-TGCTCAGGCTCAAGGCTCGTCTA-3' (SEQ ID NO:8).

Having generally described this invention, a further understanding can be obtained by reference to certain specific examples which are provided herein for purposes of illustration only and are not intended to be limiting unless otherwise specified.

EXAMPLES

1. Tissue Sampling and mRNA Isolation 1.1 Tissue Sampling and Lysis

The initial steps of library construction are best completed utilizing the usual precautions recommended for experiments carried out with RNAs (11). In addition, since library construction involves large scale PCR (Protocol 6), care is preferably taken to avoid contamination from previous libraries. Working under PCR grade conditions is especially preferred when low amounts of tissue or cells are used.

Starting from whole tissues (i.e. kidney, liver, brain, etc.), the following procedures may be routinely used. After animal anaesthesia or decapitation, the tissue is removed as quickly as possible, rapidly rinsed in ice-cold phosphate buffered saline, sliced in ~50 mg-pieces, and frozen in liquid nitrogen. The frozen sample is then ground to a fine powder under liquid nitrogen using a mortar and a pestle, transferred into Isis binding buffer (protocol 1), and homogenized with a Dounce tissue disrupter. To avoid loss of material, small samples ($\leq 20$ mg) can be transferred without previous freezing in the Isis binding buffer, and homogenized in a 1 ml Dounce. The respective amounts of tissue and lysis binding buffer suggested for a variety of conditions are indicated in Table II.

TABLE II

Small and large scale mRNA isolation and cDNA synthesis

| | | | Reaction volume ($\mu l$) | |
|---|---|---|---|---|
| Tissue/cells | Lysis binding buffer (ml) | Oligo (dT) beads ($\mu l$) | 1st strand | 2nd strand |
| 250 mg/3 × $10^7$ | 5.50 | 600 | 50 | 400 |
| 30 mg/3 × $10^6$–6 × $10^6$ | 0.70 | 100 | 50 | 400 |
| 4 mg/$10^5$–$10^6$ | 0.10 | 30 | 25 | 200 |
| 0.5 mg/3 × $10^4$–$10^5$ | 0.05–0.10 | 20 | 25 | 200 |

Starting from isolated or cultured cells, the procedure is generally much more rapid. The cell suspension, maintained in appropriate culture or survival medium, may be centrifuged at 600–1,200 g for 5 min. After supernatant removal, the lysis binding buffer is added onto the cell pellet, and the sample is homogenized by vortexing. This procedure has been successfully applied to $3 \times 10^4$–$3 \times 10^7$ cells (Table II).

1.2. mRNA Isolation.

Protocols 1–7 describe the generation of a SADE library from 0.5 mg of tissue. The amount of cDNA recovered corresponds to an experiment carried out on the mouse kidney. Slightly different amounts are expected to be obtained from other tissues, according to their mRNA content. The procedures described herein have been repeatedly used without modifications with $3 \times 10^4$–$10^5$ isolated cells. Since some applications can be performed on large amounts of tissue or cells, protocol adaptations and anticipated results for these kinds of experiments are also provided.

In the initial experiments, RNAs were extracted using standard methods (12), and poly(A) RNAs were isolated on oligo(dT) columns. Besides being time consuming, this procedure provides low and variable mRNA amounts, and cannot be easily scaled down. The alternative procedure described here (use of oligo(dT)$_{25}$ covalently linked to paramagnetic beads) is a single tube assay for mRNA isolation from tissue lysate. This procedure yields 4-times higher mRNA amounts than standard methods. Kits and helpful instructions for mRNA isolation with oligo(dT) beads can be obtained from Dynal. Handling of these beads is relatively simple, but care should be taken to avoid centrifugation, drying or freezing, since all three processes are expected to lower their binding capacity. On the other hand, beads can be resuspended by gentle vortexing or pipetting without extreme precautions.

Protocol 1. mRNA Purification

Equipment and Reagents

Appropriate tissue or cells.

Dynabead mRNA direct kit (Dynal, ref. 610-11) containing Dynabeads oligo (dT)$_{25}$, lysis binding buffer, and washing buffers.

5×reverse transcription (RT) buffer (250 mM Tris-HCl (pH 8.3), 375 mM KCl, 15 mM MgCl$_2$), provided with cDNA synthesis kit (see protocol 2).

Magnetic Particle Concentrator (MPC) for 1.5 ml tubes (Dynal, ref. 12004).

Glycogen for molecular biology (Boehringer Mannheim, ref. 901393).

Method

1. Lyse the tissue sample in 100 µl lysis binding buffer supplemented with 10 µg glycogen.
2. Add 20 µl of Dynabeads in a 1.5 ml tube and condition them according to manufacturer's instructions.
3. Using the MPC, remove the supernatant from the Dynabeads and add the tissue lysate (100 µl). Mix by vortexing and anneal mRNAs to the beads by incubating 10 min at room temperature.
4. Place the tube 2 to 5 min in the MPC and remove the supernatant. The mRNAs are fixed on the beads.
5. Using the MPC, perform the following washes (all buffers contain 20 µg/ml glycogen): twice with 200 µl washing buffer containing lithium dodecyl sulfate (LiDS), 3-times with 200 µl washing buffer, and twice with 200 µl ice-cold 1×RT buffer. Resuspend the beads by pipetting, transfer the suspension in a fresh 1.5 ml tube, wash once with 200 µl ice-cold 1×RT buffer and immediately proceed to protocol 2. mRNAs on the beads are now ready for 1st strand cDNA synthesis.

1.3 mRNA Integrity and Purity

Before generating a cDNA library, it is generally advised to check for mRNA integrity by Northern blot analysis. However, this control experiment consumes part of the material, takes several days, and often leads to ambiguous results (a variety of reasons can cause poor Northern hybridization signals). In addition, it may not be possible when using small amounts of tissue or cells. RNA degradation is generally expected only in the three following conditions: 1) cell survival is not maintained before lsis or freezing; 2) cell thawing outside of Isis buffer, and 3) use of poor quality reagents. Since Rnase-free reagents are now available from a variety of suppliers, it is much more rapid and effective to check for survival (i.e. select the appropriate culture medium) and freezing conditions than to perform tricky tests on RNA aliquots.

The purity of mRNAs isolated with oligo(dT) beads is better than that obtained with conventional methods. SAGE libraries generated using mRNAs extracted with guanidinium thiocyanate and oligo(dT) columns, provided nuclear encoded rRNAs in an amount to 1% of the sequenced tags. Using the alternative mRNA extraction procedure, rRNAs tags are no longer present in the library.

2. 1st and 2nd Strand Synthesis 2.1. 1st Strand cDNA Synthesis

The first step in the synthesis of cDNA is copying the mRNA template into complementary single-strand cDNA. In protocol 2, 1st strand cDNA is synthesized using Maloney Murine Leukaemia Virus RT (M-MLV RT). With this enzyme, SADE libraries have been generated from either large or minute amounts of cells (Table 1). In a last series of experiments, SuperScript II M-MLV RT, provided with the SuperScript cDNA synthesis kit (Life Technologies, ref. 18090-019), was used. In this case, the amount of cDNA formed (see 2.3) was increased ~4-fold. Although this better yield likely results from both the synthesis of longer cDNAs (which is not essential for the current application) and of a higher number of cDNA molecules, it is preferred to use SuperScript II M-MLV RT for very small samples (<50,000 cells). The protocol will be similar to the one described here, except for reaction volumes (20 µl for 1st strand synthesis, and 150 µl for 2nd strand synthesis).

mRNAs are generally heated 5 min at 65° C. before reverse transcription to break up secondary structures. Since such a high temperature will also denature the mRNA-oligo (dT):s hybrid samples are heated at 42° C. before initiation of 1st strand synthesis.

2.2. 2nd Strand Synthesis

Many procedures have been developed for 2nd strand cDNA synthesis. The method used here is a modification of the Grubler and Hoffman procedure. Briefly, the mRNA (in-the mRNA-cDNA hybrid) is nicked by E.coli RNAse H. E.coli DNA polymerase initiates the second strand synthesis by nick translation. E. coli DNA ligase seals any breaks left in the second strand cDNA. The procedure is described in protocol 2. This step is usually very efficient (approximately 100%) so that a 2 h-incubation period is sufficient when starting from macroamounts of material (>100 mg of tissue or $10^7$ cells).

Protocol 2. cDNA Synthesis and Cleavage

Equipment and Reagents cDNA synthesis kit (Life Technologies, ref. 18267-013) contains all buffers and enzymes necessary for first and second strand cDNA synthesis.

α[$_{32}$P]dCTP 6000 Ci/mmol (Amersham, ref. AA0075).

TEN (10 mM Tris-HCl (pH 8.0), 1 mM EDTA, 1 M NaCl).

Restriction endonuclease Sau3A I 4 U/µl (New England Biolabs, ref. 169L), provided with 10×reaction buffer and purified 100×bovine serum albumin (BSA, 10 ma/ml).

Magnetic Particle Concentrator MPC (Dynal).

Geiger counter.

Automated thermal cycler or water-baths equilibrated at 42° C., 37° C., and 16° C.

Method

1. Resuspend the beads in 12.5 µl of 1×first strand (i.e. RT) reaction buffer.
2. Incubate 2 min at 42° C.
3. Place the tube at 37° C. for 2 min. Add 12.5 µl of the following mix: 5 µl DEPC-treated water, 2.5 µl 5×first strand buffer, 1.25 µl dNTP 10 mM, 2.5 µl DTT 100 mM, 1.25 µl MMLV reverse transcriptase.
3. Incubate 1 h at 37° C. and chill on ice.
4. On ice, prepare the following mix: 169.7 µl DEPC-treated water, 4.5 µl dNTP 10 mM, 24 µl 2nd strand buffer, 2 µl α[32P]dCTP, 6 µl E.coli DNA polymerase I, 1.05 µl E.coli RNAse H. 0.75 µl E. coli DNA ligase, 2 µl glycogen 5 µg/µl.
5. Add 175 µl to the first strand tube and incubate overnight at 16° C. Keep the remaining mix for subsequent measurement of its radioactivity and calculation of dCTP specific activity.
6. Wash beads to remove non incorporated α[32P]dCTP: 4-times with 200 µl TEN+BSA[1], and 3-times with 200 µl ice-cold 1×mix Sau3A I+BSA[1]. Check with Geiger counter that the last eluate is not radioactive, whereas the material bound on the beads is highly radioactive.

[1]Final concentration of BSA: 0.1 mg/ml

7. Add on the beads the following mix: 88 µl H20, 10 µl 10×mix Sau3A I, 1 µl 100×BSA, 1 µl Sau3A I. Incubate 2 h at 37° C. Vortex intermittently.
8. Chill 5 min on ice.
9. Using the MPC, remove the supernatant, which contains the 5' end of the cDNA. Wash once with 200 µl of 1×mix Sau3A I+BSA[1]. Remove this second supernatant, pool it with the first one, and store the resulting solution (300 µl) in order to measure the yield of second strand synthesis (see text). Before going to step 10, check with Geiger counter that both the eluate and beads are radioactive.

[1]Final concentration of BSA: 0.1 mg/ml

10. Resuspend the beads in 200 µl TEN supplemented with BSA[1].

[1]Final concentration of BSA: 0.1 mg/ml 2.3. Yield of 2nd Strand Synthesis

A method to calculate the yield for first and second strand cDNA synthesis is given in the cDNA synthesis kit instruction manual. The yield of 1st strand cDNA synthesis since, as discussed above (1.3), this implies to set away part of the preparation.

Figure 2:
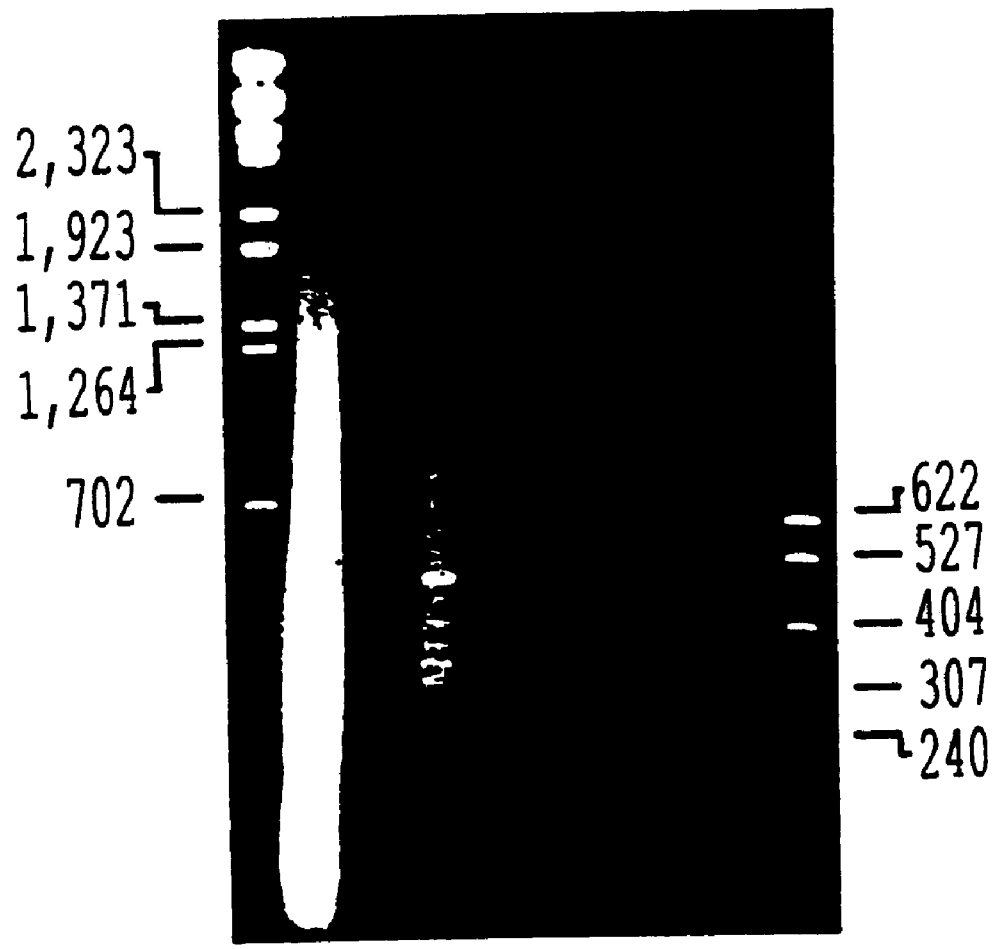
FIG. 2 is a gel analysis of cDNAs synthesized from different amounts of tissue. Poly(A) RNAs were isolated from the indicated amounts of mouse kidney, and cDNAs were synthesized and Sau3A I-digested on paramagnetic beads (see protocols 1–2). cDNAs released from beads were recovered, and half of the material obtained from each reaction was analyzed on a 1% agarose gel stained with ethidium bromide. Position of molecular weight markers are indicated in bp: left, λ Bste II-digest; right, pBR Msp I-digest.

The amount of double strand (as) cDNA formed is calculated by measuring radioactivity incorporation in the 5' end of the cDNA, which is released in the supernatant after Sau3A I digestion (see Protocol 2). The 300 µl-supernatant is extracted with PCI and the ds cDNA is ethanol precipitated in the presence of glycogen (50 µg/ml) and 2.5 M ammonium acetate. The pellet is resuspended in 8 µl of TE. Half of the material is used for liquid scintillation counting, and the remaining is loaded on a 1.0 or 1.5% agarose gel. For experiments carried out on 250, 30, 4, and 0.5 mg of mouse kidney, the following amounts were obtained (µg) of ds cDNA: 2.8, 0.3, 0.05, and 0.01. The higher amount corresponds to the incorporation of 1.3% of the input radioactivity. In these experiments, three of the four cDNA samples could be detected by ethidium bromide staining after gel electrophoresis (FIG. 2). Their size ranged between <0.2 and ~3 kbp (the small size of most cDNA fragments is due to Sau3A I digestion). When cDNA amounts are below the detection threshold of the ethidium bromide staining method, autoradiographic analysis can be performed. In this case, the gel is fixed in 10% acetic acid, vacuum dried and exposed overnight at –80° C. with one intensifying screen for autoradiography.

3. Linker Design, Preparation, and Ligation 3.1. Linker Design

A variety of linkers can be used at this point. Linkers preferably contain three important sequences: a) the appropriate anchoring enzyme overhang; b) a recognition site for a type IIs restriction enzyme (tagging enzyme); c) a priming site for PCR amplification.

Table III provides the sequence of linkers and PCR primers used. All four linkers are preferably obtained gel-purified materials. Linkers 1B and 2B display two modifications: a) 5' end phosphorylation, and b) C7 amino modification on the 3' end. Linkers phosphorylation can be performed either enzymatically with T4 polynucleotide kinase, or chemically at the time of oligonucleotide synthesis. In both cases, phosphorylation efficiency is preferably tested (Protocol 3). Chemically phosphorylated linkers were used. Linkers modification on the 3' end serves to increase the efficiency of ditag formation (protocol 5, step 8–11). Indeed, the modified 3' end cannot be blunt-ended and will not ligate to cDNA tags or linkers.

TABLE III

Sequence of linkers and PCR primers

| Oligonucleotide | Sequence | |
| --- | --- | --- |
| Linker 1A | 5'-TTTTgCCAggTCACTCAAgTCggTCATTCATgTCAgCACAgggAC-3' | (SEQ ID NO:3) |
| Linker 1Ba | 5'-gATCgTCCCTgTgCTgACATgAATgACCgACTTgAgTgACCTggCA-3' | (SEQ ID NO:4) |
| Linker 2A | 5'-TTTTTgCTCAggCTCAAggCTCgTCTAATCACAgTCggAAgggAC-3' | (SEQ ID NO:5) |
| Linker 2Ba | 5'-gATCgTCCCTTCCgACTgTgATTAgACgAgCCTTgAgCCTgAgCAA-3' | (SEQ ID NO:6) |
| Primer 1 | 5'-gCCAggTCACTCAAgTCggTCATT-3' | (SEQ ID NO:7) |
| Primer 2 | 5'-TgCTCAggCTCAAggCTCgTCTA-3' | (SEQ ID NO:8) | a Linkers 1B and 2B include two modifications (5'-phosphorylation and 3'-C7 amino modification).

With regard to the PCR priming site, it was designed with the help of Oligo™ software (Medprobe, Norway) in order to obtain PCR primers with high Tm (60° C.), and avoid self-priming or sense/antisense dimer formation. Two different priming sites must be designed in "left" and "right" linkers, otherwise the target can undergo panhandle formation, and thus escape PCR amplification.

Protocol 3. Preparing and Testing Linkers

Equipment and Reagents

Linkers 1A, 1B, 2A, and 2B at 20 pmol/µl.
Primers 1 and 2 at 20 pmol/µl.

T4 DNA ligase 1 U/μl (Life Technologies, ref. 15224-017) and 5×reaction buffer. 10 mM ATP.

PCR reagents: Taq DNA polymerase 5 U/μl (Eurobio), 10×PCR buffer (200 mM Tris-HCl (pH 8.3), 15 mM MgCl$_2$, 500 mM KCl, 1 mg/ml gelatin), 1.25 mM dNTP, 100 mM MgCl$_2$, and 100 mM DTT.

Restriction endonucleases Sau3A I (4 U/μl) and BsmF I (2 U/μl) (New England Biolabs, refs. 169L and 572L), provided with 10×reaction buffer and 100×BSA.

10-bp DNA ladder (Life Technologies, ref. 10821-015)

Automated thermal cycler and water baths equilibrated at 14° C., 37° C., and 65° C.

Tris-HCl buffered (pH 7.9) phenol-chloroform-isoamyl alcohol (PCI).

10 M ammonium acetate.

TE (10 mM Tris-HCl (pH 8.0), EDTA 1 mM).

Method

1. Mix 25 μl of linker 1A and 25 μl of linker 1B in a 0.5 ml PCR tube (final concentration: 10 pmol/μl). Proceed similarly for linkers 2A and 2B.
2. Transfer PCR tubes in the thermal cycler. Heat at 95° C. for 2 min. then let cool at room temperature for 20 min on the bench. Store at −20° C.
3. Test self-ligation of each hybrid, as well as ligation of hybrid (1A/1B) with hybrid (2A/2B). Set-up 3 ligation reactions by mixing 1 μl of hybrid (1A/1B) (tube 1), 1 μl of hybrid (2A/2B) (tube 2), 0.5 μl of hybrid (1A/1B) and 0.5 μl of hybrid (2A/2B) (tube 3) with 2 μl 10 mM ATP, 4 μl 5×ligase mix, 12 μl H$_2$O, and 1 μl T4 DNA ligase.
4. Incubate 2 h or overnight at 14° C. Analyze 10 μl aliquots on a 3% agarose gel using 10-bp DNA ladder as marker. Most of the material (≥ 80%) consists of a 94-bp DNA fragment.
5. Proceed to PCR using 105 targets from tube 3 reaction (dilute using TE buffer supplemented with 0.1 ma/ml BSA). Mix 1 μl of diluted ligation product, 5 μl 10×PCR buffer, 1 μl 100 mM MgCl$_2$, 8 μl 1.25 mM dNTP, 2.5 μl primer 1, 2.5 μl primer 2, and 30 μl water. Prepare 4 such reactions and a control tube without linker, transfer in the thermal cycler and heat at 80° C. for 2 min.
6. Add in each tube 50 μl of Taq polymerase amplification mix (5 μl 10×PCR buffer, 4 μl 100 mM DTT, 0.5 μl Taq polymerase, 40.5 μl water), and 60 μl of mineral oil if necessary for your thermal reactor.
7. Perform 29 PCR cycles (95° C., 30 s; 58° C., 30 s; 70° C., 45 s), followed by an additional cycle with a 5-min elongation time.
8. Analyze 10-μl aliquots on a 3% agarose gel. A 90-bp amplification fragment is clearly visible.
9. Pool all 4 PCR samples, extract with equal volume of PCI. Transfer the aqueous (upper) phase in a fresh tube, then add 100 μl 10 M ammonium acetate and 500 μl isopropanol. Round the tubes several times for mixing, centrifuge (15,000 g) at 4° C. for 20 min. wash twice with 400 μl 75% ethanol, vacuum dry, and resuspend the pellet in 12 μl TE buffer.
10. Set-up two 50-μl digestion reactions using 5 μl of DNA and 4 U of Sau3A I or BsmF I. Incubate 1 h at 37° C. or 65° C., as appropriate.
11. Analyze 10-μl aliquots on a 3% agarose gel. Run in parallel 1 μl of uncut PCR product. Sau3A I and BsmF I digestion must be completed to ≧80%.

3.2. Linker Preparation

It is preferable to check that ds linkers can be ligated, PCR amplified, and digested with the anchoring and tagging enzyme. Successful results with protocol 3 experiments is preferred before attempting to prepare a library. The PCR conditions described here have been optimized for Hybrid thermal reactors (TRI and Touch Down) working under control or simulated tube conditions. Different conditions may be used with other machines. Note that since the target is quite small (90 bp), elongation is performed at a relatively low temperature.

3.3. Ligating Linkers to cDNA

The concentration of ds linkers is preferably adapted to the amount of cDNA used to prepare the library. In the original protocol of Velculescu et al., 2 μg (74 pmol) of ds linkers are used. Considering that starting from 5 μg of mRNAs, 2 μg of cDNAs with 1–2 kb average size are obtained, the amount of cDNA available for ligation is in the range of 1.5–3 pmol. Since a large excess of linkers decreases the PCR signal to noise ratio, ligation is performed with 8 pmol ds linkers for libraries generated from 250 mg of tissue (~5 μg mRNAs). Starting from 5×10$^4$–10$^5$ cells (10–40 ng mRNAs), 0.5 pmol of ds linkers are used. A smaller amount of linkers may allow efficient ligation.

Protocol 4. Ligating ds Linkers to cDNA

Equipment and Reagents

Hybrid (1A/1B) and (2A/2B) at 0.5 pmol/μl, obtained from protocol 3, steps 1–2.

TEN, TE, and LoTE (3 mM Tris-HCl (pH 7.5), 0.2 mM EDTA), stored at 4° C. 10×NEB IV reaction buffer and 100×BSA (New England Biolabs).

To DNA ligase 5 U/μl (Life Technologies, ref. 15224-041) and 5×ligation mix; 10 mM ATP.

MPC (Dynal).

Water-baths equilibrated at 45° C. and 16° C.

Geiger counter

Method

1. Once the experiments described in protocol 2 have been carried out, perform 2 additional washes of the beads before ligating ds linkers to the cDNA. Using the MPC, wash the beads with 200 al of TEN+BSA[1]. Resuspend the beads in 200 μl of the same buffer (take care to recover the beads completely: mix by repeated pipetting and scrape the tube wall with the pipette tip), then separate into two 100 μl-aliquots: one will be ligated to hybrid (1A/1B), the other will be ligated to hybrid (2A/2B).

[1]Final concentration of BSA: 0.1 mg/ml

2. Add 10 μl of fresh Dynabeads in two 1.5 ml tubes. These tubes will be now treated as the two others and will be used as negative control.
3. Wash twice the 4 tubes with 200 μl of ice-cold TE buffer+BSA[1].

[1]Final concentration of BSA: 0.1 mg/ml

4. Immediately after the last rinsing, add to each tube 34 μl of the appropriate mix containing 8 μl of 5×ligase buffer and 0.5 pmol of hybrid (1A/1B) or hybrid (2A/2B). Heat 5 min at 45° C. then chill on ice.
5. Add in each tube 4 μl of 10 mM ATE, and 2 μl of T4 DNA ligase (final volume: 40 μl). Incubate overnight at 14° C.
6. Wash beads thoroughly (free linkers will poison the PCR amplification) as follows: 4-times with 200 μl of TEN+BSA[1] and 3-times with 200 μl of 1×NEBIV +BSA[1]. After the first rinsing with NEB IV, take care to resuspend completely the beads (see above) and transfer them to fresh tubes. After the last rinsing, check that radioactivity is still present on the beads, but absent from the supernatant.

[1]Final concentration of BSA: 0.1 mg/ml

7. Proceed to protocol 5 or store at 4° C.

After ligation (step 5 in protocol 4), it is very preferable to wash the beads extensively in order to remove free ds linkers. In fact, if ds linkers not ligated to cDNA fragments are not thoroughly eliminated from each sample, the library will contain large amounts (up to 25%) of linkers sequences. This may make data acquisition poorly efficient.

4. Ditags Formation

4.1. Release of cDNA Tags

Digestion with the tagging enzyme (BsmF I) will release only small DNA fragments from oligo(dT) beads. Consequently, much of the radioactivity remains bound to the beads at this stage. In order to check that extensive rinsing did not cause great loss of material, radioactivity of the beads is measured by Cerenkov counting (the data should be corrected for the efficiency of Cerenkov counting (~50% of liquid scintillation counting efficiency) after BsmF I digestion. For experiments previously described on 250, 30, 4, and 0.5 mg of mouse kidney, the amounts of ds cDNA remaining on the beads reached 450, 67, 13, and 1.8 ng, respectively. Comparison of these data with those dealing with Sau3A I-released fragments (2.3) indicates that ~6 times lower cDNA amounts are recovered on beads that on Sau3A Isupernatants. The average size of Sau3A I-cut fragments is predicted to be 256 bp. The fraction that remains bound on the beads after Sau3A I digestion thus suggests that the average length of cDNA formed is ~1.5 kb.

The whole amount of BsmF I-released material is used for ditag formation, and is, generally, not quantifed. Nevertheless, the efficiency of BsmF I digestion can be checked when ≧4 mg of tissue is used for library generation. In this case, a Geiger counter allows to detect radioactivity in the BsmF I-supernatant.

4.2. Blunt Ending of Released cDNA Tags

Different enzymes may be used for blunt ending BsmF I-released tags. In their original study, Velculescu et al. (7) carried out the blunt ending reaction with T4 DNA polymerase. In more recent applications, Klenow DNA polymerase was used (8) and is now recommended. It has been experienced that the success in library generation may be very poor using T4 DNA polymerase. This likely comes from the fact that blunt ending with T4 DNA polymerase is carried out at 11° C. (11). Such a low temperature allows protruding termini from unrelated cDNA tags to hybridize, and is thus expected to markedly decrease the amount of material available for the blunt ending reaction. Vent and sequencing grade T7 DNA polymerases has been successfully used to generate blunt ends. The procedure described in protocol 5 involves T7 DNA polymerase.

Protocol 5. Release, Blunt Ending. and Ligation of cDNA Tags

Equipment and Reagents

BsmF I, 10×NEB IV buffer and 100×BSA.

PCI.

10 M ammonium acetate.

Sequencing grade T7 DNA polymerase (Pharmacia Biotech, ref. 27098503).

5×mix salt (200 mM Tris-HCl (pH 7.5), 100 mM MgCl$_2$:, 250 mM NaCl).

2 mM dNTP. 20 T4 DNA ligase (5 U/$\mu$l) and 5×reaction buffer.

100% ethanol, 75% ethanol.

Geiger counter.

Water-baths equilibrated at 65° C., 42° C., and 16° C.

Method

1. Remove supernatant and immediately add on the beads 100 $\mu$l of the following mix: 87 $\mu$l H$_2$O, 10 $\mu$l 10×NEB IV, 1 $\mu$l 100×BSA, 2 $\mu$l BsmFI.
2. Incubate 2 h at 65° C. Vortex intermittently.
3. Chill 5 min at room temperature, collect the supernatant (which contains the ditags) and wash beads twice with 75 $\mu$l of ice-cold TE+BSA. Pool all 3 supernatants (250 $\mu$l final volume) and add 60 $\mu$g glycogen to each of the 4 reaction tubes. Measure the radioactivity still present on the beads by Cerenkov counting (see text).
4. Add 250 $\mu$l (1 volume) PCI to all 4 supernatants.
5. Vortex, then centrifuge (10,000 g) 10 min at 4° C. Transfer the upper (aqueous) phase to a fresh tube.
6. Precipitate with high ethanol concentration: add to the aqueous phase 125 $\mu$l 10 M ammonium acetate, 1.125 ml 100% ethanol, and centrifuge (15,000 g) 20 min at 4° C.
7. Wash the pellet twice with 400 $\mu$l of 75% ethanol. Vacuum dry and resuspend the pellet in 10$\mu$ LoTE.
8. Add 15 $\mu$l of 1×mix salt on each tube and heat 2 min at 42° C. Maintain tubes at 42° C. and add 25 $\mu$l of the following mix: 7.5 $\mu$l H$_2$O, 5.5 $\mu$l 100 mM DTT, 11 $\mu$l dNTP mix, 1 $\mu$l T7 DNA polymerase. Incubate 10 min at 42° C.
9. Pool together tags ligated to hybrid(1A/1B) and hybrid (2A/2B). Rinse the tubes with 150 $\mu$l LoTE+20 $\mu$g glycogen and add this solution to the pooled reactions (final volume: 250 $\mu$l). 2 tubes are obtained (1 sample, 1 negative control).
10. Extract with equal volume of PCI and high concentration ethanol precipitate (see steps 4–6). Resuspend the pellet in 6 $\mu$l LoTE.
11. Ligate tags to form ditags by adding to the 6 $\mu$l-sample: 2 $\mu$l 5×mix ligase, 1 $\mu$l 10 mM ATP, and 1 $\mu$l of T4 DNA ligase (5 U/$\mu$l). Proceed similarly for the negative control, incubate overnight at 16° C., then add 90 $\mu$l LoTE. [1]Final concentration of BSA: 0.1 mg/ml

5. PCR Amplification

Considering the linkers and primers used in studies, the desired PCR product is 110-bp long (90 bp of linkers derived sequences, and 20 bp of ditag).

5.1. PCR Buffers and Procedures

For PCR amplification of ditags, buffers and conditions different from those described by Velculescu et al. are used:

(a) amplification is performed with standard PCR buffers without DMSO and β-mercaptoethanol. Composition of the 10×PCR buffer is given in protocol 3. Promega buffer (ref. M1901) works equally well. The conditions used in the assay are as follows: 100 $\mu$M dNTP, 2.5 mM MgCl$_2$ (2 mM with Promega buffer), 0.5 $\mu$M primers, and 5 U Taq polymerase. High amounts of primers and Taq polymerase are used (standard reactions are generally performed with 0.1 $\mu$M primers and 1.25 U of enzyme) to ensure a high yield of ditags production. dNTP concentration is also slightly higher (100 vs. 50 $\mu$M) than for standard PCR amplifications. Very high dNTP concentrations should nevertheless be avoided since these are known to increase Taq polymerase-dependent misincorporations.

(b) as suggested initially (7), small scale PCR, purification of the 110-bp fragment, and then preparative PCR are performed.

5.2. Number of PCR Cycles

Figure 3:
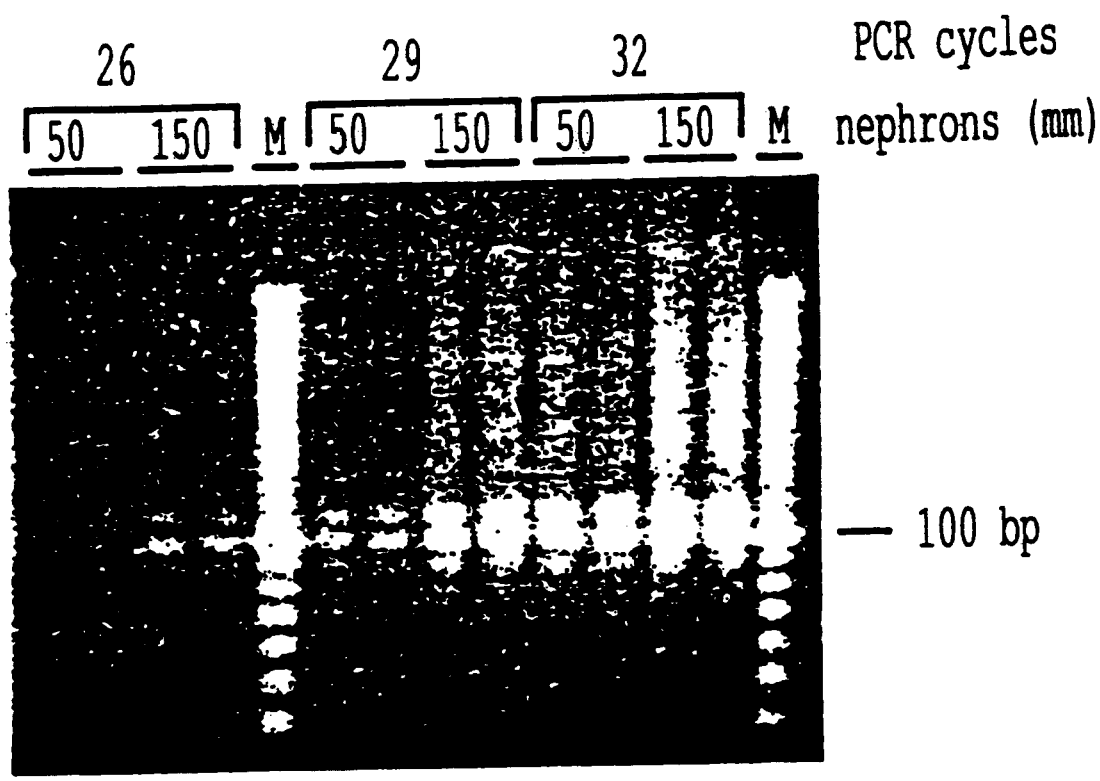
FIG. 3 shows PCR amplification of ditags. Poly(A) RNAs were isolated from 50 or 150 mm of microdissected nephron segments (corresponding to about 15,000 and 45,000 cells, respectively). The corresponding ditags were amplified by PCR using the indicated number of cycles and analyzed on a 3% agarose gel stained with ethidium bromide. The expected product (linkers+1 ditag) is 110-bp long. Molecular weight marker (M) is 10-bp DNA ladder (Life Technologies).

Before starting protocol 6, the optimal number of PCR cycles may be determined. This is best accomplished by performing duplicate PCR on 2% of the ligation product and sampling 7-μl aliquots at different cycles. The number of cycles will of course depend on the amount of starting material. For 250 mg tissue pieces, a PCR signal should be obtained with 18 cycles, and the plateau reached at 2223 cycles. The 110-bp fragment should be largely predominant (amplified products of 90 and 100 bp are not unusual). Examples of PCR carried out on ditags generated from tiny amounts of cells (15,000 to 45,000) are given in FIG. 3. Using such low amounts of cells, the 110-bp product is no longer predominant. Nevertheless, if maximal yield is achieved with less than 30 cycles (as obtained from 45,000 cells in FIG. 3), a library which is fairly representative of the tissue can be generated. Small scale PCR (10 reactions, step 1–5 in protocol 6) is performed on 2 μl and 4 lμ aliquots of ligation product for macro and microamounts of tissue, respectively.

Protocol 6. PCR Amplification of Ditags

Equipment and Reagents

Automated thermal reactor (Hybrid).

PCR reagents: Taq polymerase, Primers 1 and 2 at 20 pmol/μl, 10×PCR buffer (see protocol 3), 1.25 mM dNTP, 100 mM MgCl$_2$, and 100 mM DTT.

β-Agarase and 10×reaction buffer (New England Biolabs, ref 392L).

Sau3A I reaction buffer and 100×BSA.

Low melting point (LMP) agarose (Life Technologies, ref. 15517-022).

TBE 10× (1.12 M Tris, 1.12 M boric acid, 20 mM EDTA)

Vertical gel electrophoresis unit, with 20×20 cm plates, 1.5 mm thick spacers. and preparative comb.

10-bp DNA ladder.

Bromophenol blue loading buffer (0.125% bromophenol blue, 10% ficoll 400, 12.5 mM EDTA) filtered on 0.45-μm membrane.

Method

1. Prepare a master mix with the following reagents: 5 μl 10×PCR Buffer, 1 μl 100 mM MgCl2, 8 μl 1.25 mM dNTP, 2.5 μl primer 1, 2.5 μl primer 2, 27 μl H$_2$O (multiply these quantities by the number of reactions tubes (usually 12)). Dispense equal aliquots (46 μl) into PCR tubes and add 4 μl of DNA sample (10 tubes), negative control, or H$_2$O.
2. Transfer the tubes in the thermal reactor and heat 2 min at 80° C. (hot start conditions).
3. Add in each tube 50 μl of the following mix: 5 μl 10×PCR Buffer, 4 μl 100 mM DTT, 40 al H$_2$O, 1 μl Taq Polymerase. Add a drop of mineral oil if necessary according to the thermal cycler.
4. Perform PCR at the following temperatures: 30 sec at 94° C., 30 sec at 58° C., and 45 sec at 70° C. (27–30 cycles), followed by one cycle with an elongation time of 5 min.
5. Analyze an aliquot of each tube (7 μl) on a 3% agarose gel using 10-bp DNA ladder as marker.
6. If yield is satisfactory (see FIG. 3), pool the 10 PCR tubes in two 1.5 ml tubes. Add 30 fig glycogen in each tube, extract with PCI. Recover the aqueous phase and precipitate the DNA by centrifugation after adding 0.1 volume 3 M sodium acetate and 2.5 volumes 100% ethanol. Wash the pellet with 75% ethanol, vacuum dry, and resuspend in 300 μl LoTE. Add 75 μl of bromophenol blue loading buffer.
7. Electrophorese the PCR product through a 3% LMP agarose vertical gel (warm plates 15 min at 55° C. before pouring the gel). Run until bromophenol blue has reached bottom of the gel (~3 h).
8. Cut out the 110-bp fragment from gel and place agarose slice in a 2 ml tube. Add 0.1 volume 10×13-agarase mix, heat 10 min at 70° C., then 10 min at 40° C., and add β-Agarase (6 U/0.2 g of agarose). Incubate 1 h30 at 40° C. Add 30 μg glycogen. Extract with PCI and ethanol precipitate as indicated in section 6. Resuspend the pellet in 300 μl LoTE.
9. After determination of the optimal number of PCR cycles (usually 12), perform large scale PCR (140–150 reactions) using 2 μl of DNA and the protocol described in sections 1–4.
10. Pool PCR reactions in 2 ml tubes. Extract with PCI, ethanol precipitate (section 6) and wash the pellet twice with 75% ethanol. Resuspend the dry pellets in a final volume of 470 μl 1×mix Sau3A I.

5.3. Purification and Reamplification

The 110-bp PCR product can be purified either on a 12% polyacrylamide (7) or a 3% agarose slab gel. To avoid overloading and achieve efficient purification, pool no more than 10–12 PCR reactions on an agarose gel and slice agarose as close as possible to the 110-bp fragment. Purification and optimal number of PCR cycles should then be tested on duplicate 2 μl aliquots of the purified product. A single band of 110 bp is obtained. The absence of interference from other amplified products is essential to produce large amounts of the 110-bp fragment.

6. Ditags Isolation, Concatenation, and Cloning of Concatemers

6.1. Ditags Isolation

Two important points are addressed for ditags purification. First, since the total mass of linkers is nearly five times that of ditags, a highly resolutive polyacrylamide gel is required to thoroughly purify ditags. Second, the short length of ditags makes them difficult to detect on gel by ethidium bromide staining. This problem can be overcome by staining the gel with SYBR Green I (or equivalent products) which ensures a lower detection threshold than ethidium bromide (0.1 instead of 2 ng DNA). To obtain high sensitivity, loading buffer should not contain bromophenol blue (bromophenol blue comigrates with ditags). The gel is stained after migration in a polypropylene or PVC container.

Ditags generally do not run as a single band on polyacrylamide gel. This may come from subtle effects of base composition on electrophoretic mobility and/or some wobble for BsmF I digestion (7). All the material ranging from 22 to 26 bp is removed from the gel, The elution procedure is labor intensive but provides ditags that can be concatenated efficiently.

6.2. Concatenation

Starting from 150 PCR reactions, at least 1 μg ditags should be obtained. The optimal ligation time depends on the amount of ditags and on the purity of the preparation. Ligation is usually performed for 2 h. When yield is high (≧1.4 μg), two ligation reactions are set up, and allowed to proceed for 1 or 2 h. The corresponding concatemers are then separately purified on a 8% agarose gel.

Protocol 7. Ditags Isolation and Concatenation

Equipment and Reagents

Sau3A I, 10×reaction buffer and 100×BSA.

50×TAE (2 M Tris, 57% glacial acetic acid, 50 mM EDTA)

12% polyacrylamide gel: 53.6 ml $H_2O$, 24 ml 40% acrylamide (19:1 acrylamide:bis), 1.6 ml 50×TAE, 800 µl 10% ammonium persulfate, 69 µl TEMED. 10-bp DNA ladder.

SYBR Green I stain (FMC Bioproducts, ref 50513).

4 DNA Ligase 5 U/µl and SPOOL VALVE ligation mix; 10 mM ATP.

Vertical gel electrophoresis unit, with 20×20 cm plates, 1.5 mm thick spacers, and preparative comb.

Xylene cyanole loading buffer (0.125% xylene cyanole, 10% ficoll 400, 12.5 mM EDTA).

Spin X microcentrifuge tubes (Costar, ref. 8160)

Method

1. Save 1 µl of the 110-bp DNA fragment (section 10 of protocol 6) and digest the remaining by adding 5 µl 100×BSA and 25 µl Sau3A I. Incubate overnight at 37° C. in hot-air incubator.
2. Check for Sau3A I digestion: analyze 1 µl of uncut DNA, 1 µl and 3 µl of Sau3A I digestion (use bromophenol blue loading buffer and xylene cyanole loading buffer for uncut and Sau3A I-digested DNA, respectively) on a 3% agarose gel. Most (>80%) of the 110-bp fragment has been digested, and a faint band, corresponding to the ditags can now be detected at ~25 bp.
3. Add 125 µl xylene cyanole loading buffer to the digested DNA sample and load on a preparative 12% polyacrylamide vertical gel in 1×TAE. Run at 30 mA until bromophenol blue of the size marker is 12 cm away from the well.
4. Transfer the gel in SYBR Green I stain at 1:10,000 dilution in 1×TAE. Wrap the container in aluminum foil and stain gel for 20 min. Visualize on UV box.
5. Cut out the ditags band (24–26 bp) and transfer acrylamide slices in 0.5 ml tubes (for a 20-cm wide gel use 8 tubes). Pierce the bottom of 0.5 ml tubes with a 18 gauge needle. Place the tubes in 2 ml tubes and spin 5 min at 10,000 g. Prepare the following elution buffer for each tube: 475 µl LoTE, 25 µl 10 M ammonium acetate, 5 µg glycogen. Add 250 µl elution buffer in each 0.5 ml tube and centrifuge again. Discard 0.5 ml tubes and add 250 µl elution buffer directly in each 2 ml tube. Incubate overnight at 37° C. in hot-air incubator.
6. Prepare a series of 16 SpinX microcentrifuge tubes: add 20 µg glycogen in each collection tube. Transfer content of each 2 ml tube (~600 µl) to two SpinX microcentrifuge tubes. Spin 5 min at 13,000 g. Transfer 350 µl of eluted solution into 1.5 ml tubes (10–11 tubes), extract with PCI, perform high concentration ethanol precipitation. Wash twice with 75% ethanol, vacuum dry, and pool all pellets in 15 µl LoTE.
7. Measure the amount of purified ditags by dot quantitation (11) using 1 µl of sample. Total DNA at this stage is usually 1 µg, but a library can still be generated with 400 ng.
8. Ligate ditags to form concatemers: add to your sample (14 pi) 4.4 µl SPOOL VALVE mix ligase, 2.2 µl 10 mM ATE, and 2.2 µl concentrated (5 U/µl) T4 DNA ligase.
9. Incubate 2 h at 16° C. Stop the reaction by adding 5 µl of bromophenol blue loading buffer and store at −20° C.

6.3. Purification of Concatemers

Concatemers are heated at 45° C. for 5 min immediately before loading on gel to separate unligated cohesive ends. Concatemers form a smear on the gel from about 100 bp to several kbp (FIG. 4) and can be easily detected using SYBR Green I stain. All fragments >300 bp (i.e. with 25 or more tags) are potentially interesting for library construction. Fragments usually cut out are 350–600, 6002000, and >2000 bp and generate a first library using 600–2000 bp DNA fragments. Longer fragments will be more informative but may be cloned with poor efficiency.

Protocol 8. Purification and Cloning of Concatemers

Equipment and Reagents

SYBR Green I stain.

Vertical gel electrophoresis unit, with 20×20 cm plates, 1.5 mm thick spacers, and 20-well comb.

8% polyacrylamide gel: 61.6 ml $H_2O$, 16 ml acrylamide 40% (37.5:1 acrylamide:bis), 1.6 ml 50×TAE, 800 µl 10% ammonium persulfate, 69 µl TEMED.

100-bp DNA ladder (Life Technologies, ref.15628-019)

T4 DNA ligase 1 U/al (Life Technologies, ref. 15224-017) and SPOOL VALVE reaction buffer.

10 mM ATP.

pBluescript II, linearized with BamH I and dephosphorylated. *E. coli* XL2 Blue ultracompetent cells (Stratagene, ref. 200150).

Method

Figure 4:
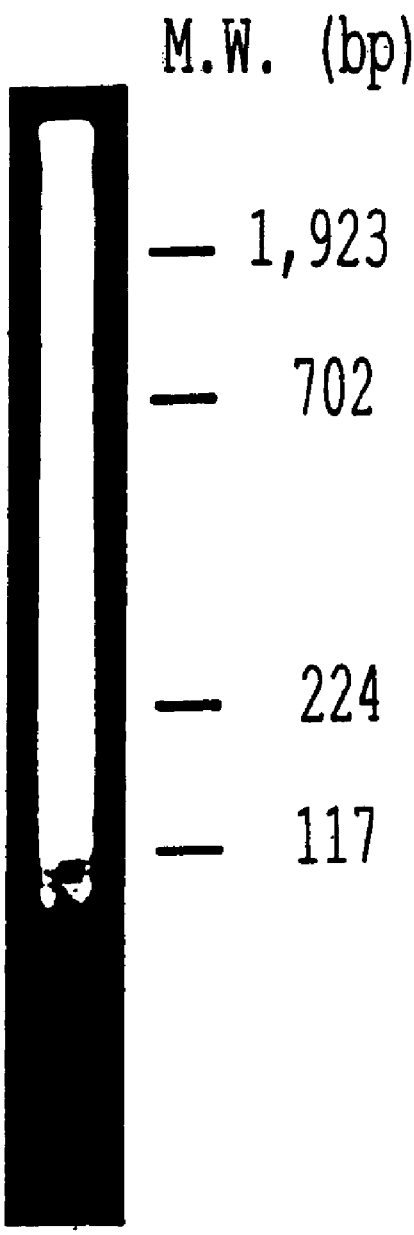
FIG. 4 shows gel analysis of concatemers. Ditags were concatenated by ligation (2 h at 16° C.), then electrophoresed through an 8% polyacrylamide gel. The gel was post-stained using SYBR Green I, and visualized by UV illumination at 305 nm. Migration of the molecular weight marker (λ BstE II-digest) is indicated on the right.

1. Heat sample 5 min at 45° C. and load into one lane of a 20 wells 8% acrylamide gel. Run at 30 mA until bromophenol blue is 10–12 cm from the well.
2. Stain the gel with SYBR Green I as described in protocol 7 and visualize on UV box.
3. Concatemers form a smear on gel with a range from about 100 bp to the gel well (FIG. 4). Cut out regions containing DNA of 350–600, 600–2000, and >2000 bp. Purify separately DNA of each three slices as described in section 5–6 of protocol 7 (a 1-h incubation period of gel slices in LoTE/ammonium acetate solution is sufficient). Resuspend the pellet in 6 µl LoTE and generate a first library using concatemers of 600–2000 bp.
4. Mix 6 µl; of concatemers and 2 µl (25 ng) of BamH I-cut pBluescript II. Heat 5 min at 45° C. then chill on ice.
5. Add 3 µl SPOOL VALVE mix ligase, 1 µl $H_2O$, 1.5 µl 10 mM ATP, and 1.5 µl T4 DNA ligase (1 U/µl). Mix and incubate overnight at 16° C.
6. Add 20 µg glycogen and 285 µl LoTE and extract with PCI. Ethanol precipitate, wash twice with 75% ethanol, vacuum dry, and resuspend the pellet in 12 µl LoTE.
7. Transform *E. coli* XL2 Blue ultracompetent cells with 1/3 (4 µl) of ligation reaction according to the manufacturer's instructions. Plate different volumes (5 µl, 10 µl, 20 pl, 40 µl) of transformation mix onto Petri dishes containing Luria agar supplemented with ampicillin, X-gal, and IPTG. Incubate 15–16 hr at 37° C. Save the remaining (~900 µl) transformation solution (add 225 µl 80% glycerol, mix intermittently for 5 min. and store at −80° C.). It will be used to plate additional bacteria if library appears correct.
8. Count insert-free (i.e. blue) and recombinant (i.e. white) bacterial colonies on each plate. The fraction of recombinant colonies should be >50%, and their total number should be in the range of 10,000–60,000 for 1 ml of transformation mix.

6.4. Cloning of Concatemers

Concatemers can be cloned and sequenced in a vector of choice. Concatemers are cloned in pBluescript II linearized with BamH I and dephosphorylated by calf intestinal alkaline phosphatase treatment. Any kind of vector with a BamH I site in the multiple cloning site will be suitable. Velculescu et al. (7, 8) use pZero-1 from Invitrogen which only allows recombinants to grow (DNA insertion into the multiple cloning site disrupts a lethal gene). The competent cells and transformation procedures (heat shock or electroporation) can also be changed according to your facilities. Whatever is chosen, it is preferable to use bacterial cells allowing very high cloning efficiency ($\geq 5 \times 10^9$ transformants/µg of supercoiled DNA). An important point is to evaluate the number of clones (protocol 8, step 8) obtained in the library. Since a large number (1,000–2,000) of clones will be sequenced, the total number of recombinants should be >10,000.

Library screening can be performed by PCR or DNA miniprep. DNA miniprep may provide more reproducible amounts of DNA than PCR, and avoids false positive signals. Qiaprep 8 miniprep kit (Qiagen, ref. 27144) may be used, which enables performing 96 minipreps in ~2 hours. Plasmid DNA is eluted from Qiagen columns with 100 µl of elusion buffer; 5 µl are digested to evaluate insert size, and if insert is >200 bp, 5 µl are directly used for DNA sequencing.

7. Data Analysis

7.1. Software

Once cloned concatemers have been sequenced, tags may be extracted, quantified, and identified through possible data bank matches. Two softwares have been written to perform these tasks.

SAGE software (7) was written in Visual Basic and operates on personal computers through the Microsoft Windows system. It extracts tags from text sequence files, quantify them, allows to compare several libraries, and provides links to GenBank data downloaded from CD-ROM flat files or over the Internet. The latter function enables rapid identification of tags originating from characterized genes or cDNAs. However, description of EST sequences is truncated, which constrains to look for individual GenBank reports. SAGE software also includes several simulating tools which allows, for example, to assess the significance of differences observed between two libraries, and to evaluate the sequencing accuracy.

The second software is currently developed at the University of Montpellier-2 (France) by J. Marti and co-workers, as part of a database (CbC, for Cell by Cell) intended to store and retrieve data from SAGE experiments. Scripts for extraction of data are developed in C language under Unix environment and the database management system implemented in Access®. Text files are concatenated to yield the working file from which tag sequences are extracted and enumerated. Treatment of raw data involves identification of vector contaminants, truncated and repeated ditags (see below). For experiments on human, mouse and rat cell samples, the tags are searched in the non-redundant set of sequences provided by the UniGene collection. These data can be loaded from the anonymous FTP site: ncbi.nlm.gov/repository/unigene/. Useful files are Hs.data.Z and Hs.seq.uniq.Z for man, and similar files for mouse and rat. The results are displayed in a table which provides the sequence of each tag, its number of occurrences with the matching cluster number (Hs# for *homo sapiens*, Mm# for *Mus musculus* and Rn# for *Rattus norvegicus*), and other data extracted from the source files, including GenBank accession numbers. For human genes, when available, a link is automatically established with GeneCards, (http://bioinfo.weizmann.ac.il/cards/) allowing to get additional information.

The contents of both of these software packages are incorporated herein by reference in their entirety.

7.2. Library Validity

7.2.1. Inserts Length

Initial assessment of library quality will be obtained from screening for inserts length. A good library should contain >60% clones with inserts $\geq$240 bp (20 tags). Only one DNA strand is sequenced, since accuracy is obtained from the number of tags recorded, rather than from the quality of individual runs. Depending on budget and sequencing facilities, either all clones or only the most informative ones will be sequenced. It should be noted that the average length of inserts does not fit with that of gel-purified concatemers. Although 600–2000 bp long concatemers are usually extracted, most of the clones have inserts <600 bp, and inserts >800 bp are generally not obtained. A number of reasons can explain such a paradoxical result. Indeed, long inserts are known to be cloned with poor efficiency. In addition, they are expected to contain several repeats or inverted repeats, and may thus form unstable plasmid constructs. Supporting this interpretation, it has been demonstrated (14), and it has also been observed, that efficient removal of linkers (which represents up to 20% of total tags in poor libraries) increases the average length of cloned inserts. At any rate, it is worth to emphasize that similar biological information is obtained from libraries with short and long inserts.

7.2.2. Gene Expression Pattern

The basic pattern of gene expression in eukaryotic cells have been established long ago by kinetics analysis of mRNA-cDNA hybridization (15, 16). In a "typical" mammalian cell, the total RNA mass consists of 300,000 molecules, corresponding to ~12,000 transcripts which divide into three abundance classes. A very small number of mRNAs (~10) are expressed to exceedingly high levels (3,000 15,000 copies/cell). A larger number of mRNAs (~500) reaches an expression level in the range of 100–500 copies/cell. Finally, the majority of mRNAs (>10,000) are poorly expressed (10–100 copies/cell). This basic pattern should be observed in SAGE or SADE libraries. However, before translating tags abundance in a definite gene expression profile, the data should preferably be scrutinized for artefacts encountered in library construction.

7.2.3. Occurrence of Linker-derived Sequences

As mentioned above, some libraries display a high amount of linker sequences. If this amount is 20% or more, sequencing will be quite expensive, and it is better to start again from the RNA sample. Library contamination with 10–15% of linker sequences is acceptable, 5–10% is good, and <5% is excellent. In addition to the two perfect linker matches (GTCCCTGTGC (SEQ ID NO:27), and GTCCCTTCCG (SEQ ID NO:28)), reading ambiguities can lead to sequences with one mismatch. These linker-like sequences are also easily identified since, assuming efficient enzymatic cleavage, the probability of having adjacent Sau3A I and BsmF I sites in the concatemers is normally zero. Linker and linker-like sequences can be automatically discarded using SAGE or CbC software, and their relative amounts can be used to evaluate the sequencing accuracy (see 7.1.).

7.2.4. Duplicate Ditags

Another category of sequences that may be deleted are those corresponding to duplicate ditags. Indeed, except for peculiar tissues (e.g. lactating gland or laying hen oviduct) in which one or a very small number of transcripts constitutes the bulk of the mRNA mass, the probability for any two tags to be found several times in the same ditag is very small. Elimination of repeated ditags will therefore correct for preferential PCR amplification of some targets, and for picking several bacterial colonies originating from the same clone. Most ditags (>95%) generally occur only once when the library is constructed from macroamounts of tissue. For microlibraries, the percent of unique ditags is generally lower. When it is no longer compatible (<75%) with efficient data acquisition, it is recommended to start again from the first (small scale) PCR (see protocol 6). Duplicate ditags are automatically retrieved from the sequence files by SAGE and CbC softwares.

7.3. Number of Tags to be Sequenced

The number of tags to be analyzed will obviously depend on the application and tissue source. As a matter of fact, reducing the tissue complexity through isolation of defined cell populations will allow to markedly diminish the minimum number of tags for accurate analysis, and to better correlate molecular and physiological phenotypes.

Figure 5:
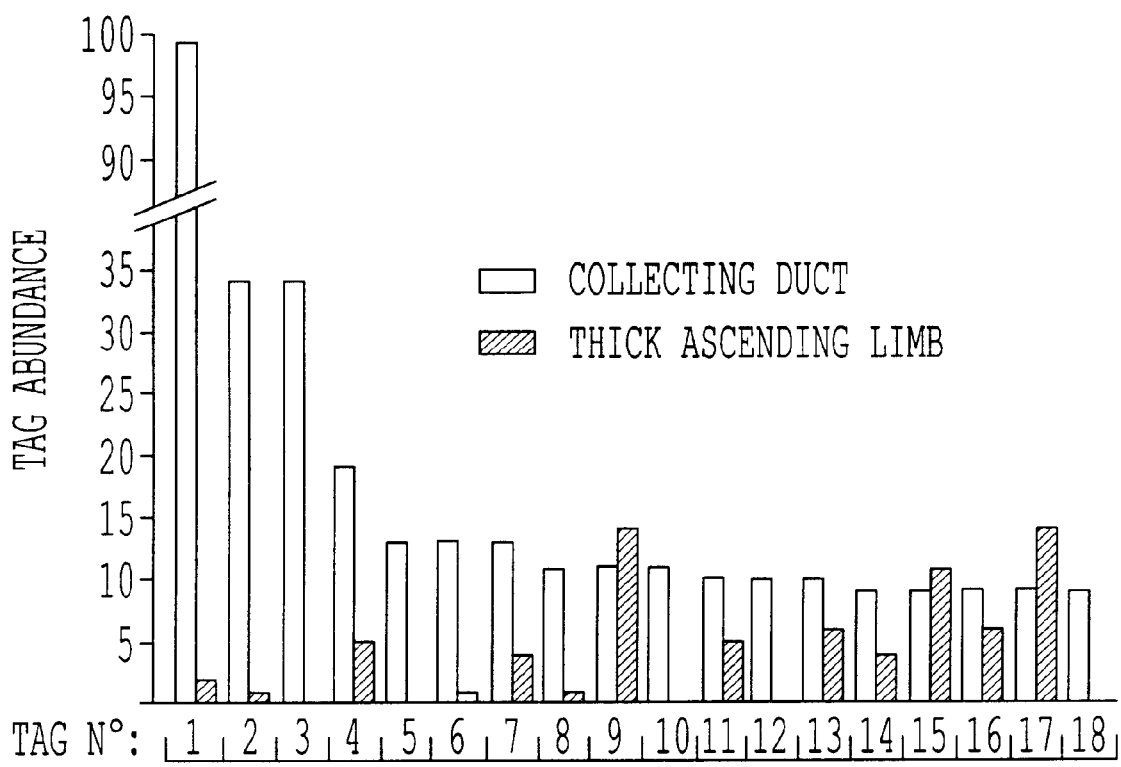
FIG. 5 is a comparison of gene expression levels in two nephron portions of the mouse kidney. SADE libraries were constructed from ~50,000 cells isolated by microdissection from medullary collecting ducts or medullary thick ascending limbs, and 5,000 tags were sequenced in each case. The data show the 18 most abundant collecting duct tags originating from nuclear transcripts (mitochondrial tags were excluded from the analysis), and their corresponding abundance in the thick ascending limb library.

Delineation of the most expressed genes (>500 copies/cell) in one tissue, and comparison with their expression level in another one, will require to sequence only a few thousand tags (FIG. 5). Analyzing 5,000 tags, 300 will be detected at least 3 times. Since automated sequencers can read 48–96 templates simultaneously, 10,000 tags will be recorded from 5–10 gels if the average number of tags/clone is ~20.

The most difficult projects may be those aiming to compare gene expression profiles in the same tissue under two physiological or pathological conditions. Differentially expressed genes could belong to any of the three abundance classes and, furthermore, they can be either up- or down-regulated. A reasonable number of tags to be sequenced would be in the range of 30,000–50,000. The probability (P) of detecting a sequence of a given abundance can be calculated from the Clarke and Carbon (16) equation ($N=\ln(1-P)/\ln(1-x/n)$), where N is the number of sequence analyzed, x is the expression level, and n is the total number of mRNAs per cell (~300,000). Thus, the analysis of 30,000 and 50,000 tags will provide a 95% confidence level of detecting transcripts expressed at 30 and 18 copies/cell, respectively. Most up-regulation processes will be therefore assessed. For example, tags corresponding to poorly expressed transcripts may be detected 1 and 2 5 times in control and experimental conditions, respectively. However, one should be aware that the possibility of assessing down-regulation processes will be less exhaustive. It will only concern tags present >5–10 times in the control condition, which excludes from the analysis part of the poorly expressed transcripts.

In Table I above, which corresponds to the characterization of the most abundant nuclear transcripts in the mouse outer medullary collecting duct (OMCD) and establishes their differential expression in the medullary thick ascending limb (MTAL), the two left columns correspond to the data illustrated in FIG. 5, and provide the abundance of each tag in the two libraries. The third column provides the sequence of the tags. The right column indicates results of individual BLAST search in Genank, carried out using a 14-bp sequence (the Sau3 A I recognition sequence, plus the 10 bp specific for each tag).

Obviously, numerous modifications and variations of the present invention are possible in light of the above teachings. It is therefore to be understood that within the scope of the appended claims, the invention may be practiced otherwise than as specifically described herein.

European Patent Application Serial No. 99-400189.9, filed on Jan. 27, 1999, is incorporated herein by reference.

REFERENCES

1. DeRisi, J. L., Vishwanath, R. Y., and Brown, P. O. (1997). *Science*, 278, 680.
2. Wodicka, L., Dong, H., Mittmann, M., Ho, M. H., and Lockhart, D. J. (1997). *Nature Biotechnology*, 15, 1359.
3. Gress, T. M., Hoheisel, J. D., Lennon, G. G., Zehetner, G., and Lehrach, H (1992). *Mamm. Genome*, 3, 609.
4. Piétu, G., Alibert, A., Guichard, V., Lamy, B., Bois, F., et al. (1996). *Genome Research*, 6, 492.
5. Adams, M. A., Kerlavage, A. R., Fleischmann, R. D., Fuldner, R. A., Bult, C. J., et al. (1995). *Nature*, 377 (No. 6547S), 3.
6. Okubo, K., Hori, N., Matoba, R., Niiyama, T., Fukushima, A., et al. (1992). *Nature Genet.*, 2, 173.
7. Velculescu, V. E., Zhang, L., Vogelstein, B., Kinzler, K. W, (1995). *Science*, 270, 484.
8. Velculescu, V. E., Zhang, L., Zhou, W., Vogelstein, J., Basrai, M., et al. (1997). *Cell*, 88,243.
9. Zhang, L., Zhou, W. Velculescu, V. E., Kern, S. E., Hruban, R. H., et al. (1997). *Science*, 276, 1268.
10. Polyak, K., Xia, Y., Zweier, J. L., Kinzler, K. W., and Vogelstein, B. (1997). *Nature*, 389, 300.
11. Ausubel, F. M., Brent, R., Kingston, R. E., Moore, D. D., Seidman, J. G., et al. (1993, updated quaterly). *Current protocols in Molecular Biology*. Greene Publishing Associates and Wiley-Interscience, New York.
12. Chomczynski, P., and Sacchi, N. (1987). *Anal. Biochem.*, 162, 156.
13. Powell, J. (1998). *Nucleic Acids Res.*, 26, 3445.
14. Hastie, N. D., and Bishop, J. O. (1976) *Cell*, 9, 761.
15. Hereford, L. M., and Rosbash, M. (1977). *Cell*, 10,453.
16. Clarke, L., and Carbon, J. (1976). *Cell*, 9, 91.

All of the publications listed above are incorporated herein by reference.

What is claimed is:

1. A method of obtained a library of tags capable of defining a specific state of a biological sample, comprising:

(1) extracting mRNA from a biological sample comprising $\leq 5 \times 10^6$ cells, corresponding to at most 50 µg of total RNA or 1 µg of poly(A) RNA, by contacting the biological sample with an oligo(dT) covalently bound to paramagnetic beads, (2) generating a double-strand cDNA library from the extracted mRNA according to a process comprising:

(a) synthesizing the $1^{st}$ strand of the cDNA by reverse transcription of the mRNA template into a $1^{st}$ complementary single-strand cDNA, using a reverse transcriptase lacking Rnase H activity, and (b) synthesizing the $2^{nd}$ strand of the cDNA by nick translation of the mRNA in the mRNA-cDNA hybrid form by an *E. coli* DNA polymerase, (3) cleaving the cDNAs with the restriction endonuclease Sau3A I as an anchoring enzyme, (4) separating the cleaved cDNAs in two aliquots, (5) ligating the cDNA contained in each of the two aliquots via the Sau3A I restriction site two different hybrid DNA molecules composed from linkers 1A and 1B or from linkers 2A and 2B, wherein the linkers have the following formulas:

SEQ ID NO:3,

SEQ ID NO:4,

SEQ ID NO:5, or

SEQ ID NO:6, (6) digesting the products obtained in step (5) with a BsmF I restriction enzyme, to obtain two different tags, (7) blunt-ending the tags with a DNA polymerase, and mixing the tags ligated with the different linkers, (8) ligating the tags obtained in step (7) with a DNA ligase, to form ditags, and (9) determining the nucleotide sequence of at least one tag of the ditags.

2. The method of claim 1, wherein the biological sample is a tissue sample or a cell culture.

3. The method of claim 1, wherein the DNA polymerase is a T7 DNA polymerase or a Vent polymerase.

4. The method of claim 1, wherein the oligo(dT) is an oligo(dT)$_{25}$.

5. The method of claim 1, wherein in step (1), after mRNA binding to beads, different washes are performed in washing buffer supplemented with glycogen.

6. The method of claim 1, wherein the two different oligonucleotide linkers further comprise amplification primer hybridization sequences, the method further comprises amplifying the ditags.

7. The method of claim 6, wherein the ditags are amplified with primers having the following formula:

SEQ ID NO:7 and

SEQ ID NO:8.

8. The method of claim 1, wherein step (9) further comprises producing and cloning concatemers of the ditags.

9. The method of claim 5, wherein the concatemers of the ditags have more than 300 bp.

10. The method of claim 1, wherein the biological sample is from nephron segments and contains about 15,000 to 45,000 cells, corresponding to 0.15–0.45 μg of total RNA.

11. The method of claim 1, wherein in step (2) the synthesis of the $1^{st}$ strand of a cDNA is performed with Moloney Murine Leukaemia Virus reverse transcriptase (M-MLV RT), and oligo(dT)$_{25}$ as primers.

12. The method of claim 1, wherein the amount of each linker in step (5) is at most 8–10 pmol and comprised between 0.5 pmol and 8 pmol for initial amounts of respectively 10–40 ng of mRNAs and 5 μg of mRNAs.

13. A method of obtaining a library of tags able to define a specific state of biological sample, comprising:

(1) extracting mRNA from biological sample comprising $\leq 5 \times 10^6$ cells, corresponding to at most 50 μg of total RNA or 1 μg of poly(A) RNA, by contacting the biological sample with an oligo(dT) covalently bound to paramagnetic beads, (2) generating a double-strand cDNA library from the extracted mRNA according to a process comprising:

(a) synthesizing the $1^{st}$ strand of the cDNA by reverse transcription of the mRNA template into a $1^{st}$ complementary single-strand cDNA, using a reverse transcriptase lacking Rnase H activity, and (b) synthesizing a $2^{nd}$ strand of the cDNA by nick translation of the mRNA in the mRNA-cDNA hybrid-form by an *E. coli* DNA polymerase, (3) cleaving the cDNAs with the restriction endonuclease Sau3A I as an anchoring enzyme, (4) separating the cleaved cDNAs in two aliquots, (5) ligating the cDNA contained in each of the two aliquots via the Sau3A I restriction site to a linker consisting of one double-strand cDNA molecule composed from linkers 1A and 1B or from linkers 2A and 2B. wherein the linkers have the following formulas:

SEQ ID NO:3,

SEQ ID NO:4,

SEQ ID NO:5, or

SEQ ID NO:6, (6) digesting the products from step (5) with a tagging enzyme BsmF I and releasing linkers with an anchored short piece of cDNA corresponding to a transcript-specific tag, the digestion generating BsmF I tags specific of said mRNA, (7) blunt-ending the BsmF I tags with a DNA polymerase and mixing the tags ligated with the different linkers, (8) ligating the tags obtained in step (7) to form ditags with a DNA ligase, and (9) amplifying the tags obtained in step (8) with primers comprising 20–25 bp and having a Tm of 55°–65° C.

(10) isolating the ditags having between 20 and 28 bp from amplification products obtained in step (9) by digesting the amplification products with the anchoring enzyme Sau3A I and separating the digested products by gel electrophoresis,

(11) ligating the ditags obtained in step (10) to form concatemers, purifying the concatemers, and separating the concatemers having more than 300 bp,

(12) cloning and sequencing the concatemers, and

(13) analyzing the tags.

14. The method of claim 13, wherein the biological sample is a tissue sample or a cell culture.

15. The method of claim 13, wherein the DNA polymerase is a T7 DNA polymerase or a Vent polymerase.

16. The method of claim 13, wherein the oligo(dT) is as oligo(dT)$_{25}$.

17. The method of claim 13, wherein the primers of step (9) have the following formulas:

SEQ ID NO:7 and

SEQ ID NO:8.

18. The method of claim 13, wherein the tissue sample is from nephron segments and contains about 15,000 to 45,000 cells, corresponding to 0.15–0.45 μg of total RNA.

19. The method of claim 13, wherein in step (1), after mRNA binding to beads, different washes are performed in washing buffer supplemented with glycogen.

* * * * *

UNITED STATES PATENT AND TRADEMARK OFFICE
CERTIFICATE OF CORRECTION

PATENT NO. : 6,506,561 B1
DATED : January 14, 2003
INVENTOR(S) : Lydie Cheval et al.

It is certified that error appears in the above-identified patent and that said Letters Patent is hereby corrected as shown below:

<u>Column 31,</u>
Line 62, "A method of obtained" should read -- A method of obtaining --.

Signed and Sealed this

Twenty-fourth Day of February, 2004

JON W. DUDAS
*Acting Director of the United States Patent and Trademark Office*